US008546133B2

(12) United States Patent
Licamele et al.

(10) Patent No.: US 8,546,133 B2
(45) Date of Patent: *Oct. 1, 2013

(54) SYSTEMS AND METHODS FOR CONTAMINANT REMOVAL FROM A MICROALGAE CULTURE

(75) Inventors: Jason Licamele, Scottsdale, AZ (US); Anna Lee Y. Tonkovich, Gilbert, AZ (US); Aniket Kale, Chandler, AZ (US); Alexander Sitek, Gilbert, AZ (US); Scott Kuhlman, Tempe, AZ (US)

(73) Assignee: Heliae Development LLC, Gilbert, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/535,055

(22) Filed: Jun. 27, 2012

(65) Prior Publication Data
US 2013/0164836 A1 Jun. 27, 2013

Related U.S. Application Data

(60) Provisional application No. 61/578,533, filed on Dec. 21, 2011.

(51) Int. Cl.
*C12M 1/00* (2006.01)
*C12M 3/00* (2006.01)
(52) U.S. Cl.
USPC ......... 435/308.1; 435/134; 435/393; 210/704
(58) Field of Classification Search
USPC ............... 435/134, 303.1, 303.8, 393, 292.1; 209/164, 168; 210/262, 703–707, 601, 608, 210/672
See application file for complete search history.

(56) References Cited

U.S. PATENT DOCUMENTS

| | | | |
|---|---|---|---|
| 3,642,617 A | 2/1972 | Brink et al. |
| 3,957,017 A | 5/1976 | Carmignani et al. |
| 3,965,007 A | 6/1976 | Conn et al. |
| 3,969,336 A | 7/1976 | Criswell |
| 3,994,811 A | 11/1976 | Cohen et al. |
| 4,267,038 A | 5/1981 | Thompson |
| 4,399,028 A | 8/1983 | Kile et al. |
| 4,613,430 A | 9/1986 | Miller |
| 4,613,431 A | 9/1986 | Miller |
| 4,764,311 A | 8/1988 | Klaes |

(Continued)

FOREIGN PATENT DOCUMENTS

| WO | 03/022041 A1 | 3/2003 |
|---|---|---|
| WO | 2005058760 A1 | 6/2005 |

(Continued)

OTHER PUBLICATIONS

A.A. Al-Shamrani et al., Separation of oil from water by dissolved air flotation, A: Physicochemical and Engineering Aspects 209 (2002) pp. 15-26.

(Continued)

*Primary Examiner* — Michael Hobbs
(74) *Attorney, Agent, or Firm* — The Noblitt Group, PLLC

(57) ABSTRACT

Systems and methods for the removal of contaminants from a liquid culture microalgae and/or cyanobacteria comprise an inlet tube, a pump, a gas injector, a vertical chamber, and/or a collection container that promotes the production of foam in the microalgae culture, wherein the foam contains the contaminants.

19 Claims, 12 Drawing Sheets

(56) References Cited

U.S. PATENT DOCUMENTS

| | | | |
|---|---|---|---|
| 4,913,805 | A | 4/1990 | Chin |
| 5,078,867 | A | 1/1992 | Danner |
| 5,282,962 | A | 2/1994 | Chen |
| 5,380,160 | A | 1/1995 | Chen |
| 5,484,525 | A | 1/1996 | Mowka, Jr. |
| 5,562,821 | A | 10/1996 | Gutierrez-Collazo |
| 5,665,227 | A | 9/1997 | Watt |
| 5,728,304 | A | 3/1998 | Yeh |
| 5,800,704 | A | 9/1998 | Hansen |
| 5,951,875 | A | 9/1999 | Kanel et al. |
| 6,000,551 | A | 12/1999 | Kanel et al. |
| 6,156,209 | A | 12/2000 | Kim |
| 6,303,028 | B1 | 10/2001 | Marks et al. |
| 6,436,295 | B2 | 8/2002 | Kim |
| 6,524,486 | B2 | 2/2003 | Borodyanski et al. |
| 6,808,625 | B1 | 10/2004 | Wu |
| 7,033,506 | B2 | 4/2006 | LeJeune |
| 7,264,714 | B2 | 9/2007 | Joneid |
| 7,445,706 | B2 | 11/2008 | Liu |
| 7,624,969 | B2 | 12/2009 | Schletz et al. |
| 7,785,476 | B2 | 8/2010 | Newman |
| 7,867,386 | B2 | 1/2011 | Tunze et al. |
| 2003/0201232 | A1 | 10/2003 | Cheyne |
| 2004/0026322 | A1 | 2/2004 | Nussbaumer et al. |
| 2006/0180533 | A1* | 8/2006 | Cummins ............... 210/169 |
| 2007/0193955 | A1 | 8/2007 | Nelson |
| 2008/0023407 | A1 | 1/2008 | Eriksson et al. |
| 2009/0008325 | A1 | 1/2009 | Ju et al. |
| 2010/0050502 | A1 | 3/2010 | Wu et al. |
| 2010/0051520 | A1 | 3/2010 | Marks et al. |
| 2010/0096307 | A1 | 4/2010 | Weidl |
| 2010/0120643 | A1 | 5/2010 | Brown et al. |
| 2010/0176062 | A1 | 7/2010 | Kanel et al. |
| 2010/0181234 | A1 | 7/2010 | Clayton et al. |
| 2010/0297714 | A1 | 11/2010 | Ju |
| 2010/0305227 | A1 | 12/2010 | Parker et al. |
| 2011/0000854 | A1 | 1/2011 | Nichols et al. |
| 2011/0076748 | A1 | 3/2011 | Salvo et al. |
| 2012/0129244 | A1 | 5/2012 | Green et al. |

FOREIGN PATENT DOCUMENTS

| | | |
|---|---|---|
| WO | 2005123598 A1 | 12/2005 |
| WO | 2008156835 A2 | 12/2008 |
| WO | 2009088839 A2 | 7/2009 |
| WO | 2010017243 A1 | 2/2010 |
| WO | 2010036334 A1 | 4/2010 |
| WO | 2010123848 A2 | 10/2010 |

OTHER PUBLICATIONS

AquaC, Inc, AquaC protein skimmer user manual, U.S. Patent, 2005, San Diego, CA.

Kari J.K. Attramadal et al., The effects of moderate ozonation or high intensity UV-irradiation on the microbial environment in RAS for marine larvae, Aquaculture 330-333 (2012) pp. 121-129.

Anders S Carlsson et al., Micro- and Macro-Algae: Utility for industrial applications, EPOBIO project, Sep. 2007, CNAP, University of York.

Chun-Yen Chen et al., Cultivation, photobioreactor design and harvesting of microalgae for biodiesel production: A critical review, Bioresource Technology 102 (2011) pp. 71-81.

Ya-Ling Cheng, Dispersed ozone flotation of *Chlorella vulgaris*, Bioresource Technology 101 (2010) pp. 9092-9096.

Ya-Ling Cheng, Harvesting of *Scenedesmus obliquus* FSP-3 using dispersed ozone flotation, Bioresource Technology 102 (2011) pp. 82-87.

Logan Christenson and Ronald Sims, Production and harvesting of microalgae for wastewater treatment, biofuels, and bioproducts, Biotechnology Advances 29 (2011) pp. 686-702.

Andrew Csordas and Jaw-Kai Wang, An integrated photobioreactor and foam fractionation unit for the growth and harvest of *Chaetoceros* spp. in open systems, Aquacultural Engineering 30 (2004) pp. 15-30.

L. Gouveia et al., Microalgae in Novel Food Products, Food Chemistry Research Developments, 2008.

Rita Henderson, Simon A. Parsons, Bruce Jefferson, The impact of algal properties and pre-oxidation on solid-liquid separation of algae, Wat er Re s e arch 42 (2008) 1827-1845.

Joseph D. Henry, Jr., Ph.D., P.E., et al., Alternative Separation Processes.

Akshaya Jena and Krishna Gupta, Characterization of Water Vapor Permeable Membranes, Ithaca, NY.

Jonathant, Benefits of a Protein Skimmer, livestrong.com, Jun. 14, 2011.

Richard M. Knuckeya et al., Production of microalgal concentrates by flocculation and their assessment as aquaculture feeds, Aquacultural Engineering vol. 35, Issue 3 , Oct. 2006, pp. 300-313.

Nasir Kureshy, D. Allen Davis, and C.R. Arnold, Effect of Ozone Treatment on Cultures of *Nannochloropsis oculata, Isochrysis galbana*, and *Chaetoceros gracilis*, Journal of the World Aquaculture Society, vol. 30, No. 4, Dec. 1999, pp. 473-180.

Robert Lemlich, Adsorptive Bubble Separation Methods Foam Fractionation and Allied Techniques, Industrial and Engineering Chemistry, vol. 60, No. 10, Oct. 1968, pp. 16-29.

L. Gouveia et al., Microalgae in Novel Food Products, Food Chemistry Research Developments, 2008, pp. 1-37.

RK2 Systems, Inc., Aquaculture Protein Fractionator RK2Systems Inc RK75PE HDPE Molded Tank, 2001.

Glenn Schipp and Damon Gore, Recirculating Marine Aquaculture Systems, Report on an ISS Institute/ DEST Overseas Travel Fellowship, Aug. 2006, pp. 4-86.

The Ozone, pp. 35-60.

John H. Tullock, Algae Control in the Marine Aquarium, http://www.amdareef.com/ho_algae.htm, 2001-2003.

Nyomi Uduman, Dewatering of microalgal cultures: A major bottleneck to algae-based fuels, AIP Journal of Renewable and Sustainable Energy 2, 2010.

Protein Skimmer, http://www.algone.com/aquarium-articles/saltwater-aquarium/protein-skimmer, Nov. 2011.

James Hanotu et al., Microflotation Performance for Algal Separation, pp. 1-21.

\* cited by examiner 8A  8B

11A

11B

11C

SYSTEMS AND METHODS FOR CONTAMINANT REMOVAL FROM A MICROALGAE CULTURE

CROSS-REFERENCES TO RELATED APPLICATION

This application claims the benefit of U.S. Provisional Patent Application No. 61/578,533, filed Dec. 21, 2011, and incorporates the disclosure of the application by reference.

BACKGROUND

Microalgae cultures within a growing vessel comprise a number of undesirable contaminant or foreign substances besides the primary algae type intended to be grown and harvested. These undesirable substances may comprise pollutants, growth inhibitors, predators, competitors, detritus, dirt and other suspended or settled solids, and clumped algae. The growth inhibitors may comprise, but are not limited to, algae metabolites, cell debris, bacteria, coliform bacteria, fungi, detrital matter, dissolved organic matter, fecal matter, and other micro-particles. The competitors and predators may comprise an invasive algae type other than the primary algae type of the culture, and zooplankton that feed on phytoplankton.

The growth of algae in terrestrial systems such as open ponds or bioreactors may be improved by removing contaminants from the algae culture. Removal of contaminants from the algae culture may enhance the growth rate and health of the algae culture due to a decrease in competition for nutrients, gases, and light, and a decrease in substances that are directly and/or indirectly harmful, toxic, or poisonous to the primary algae type.

SUMMARY

Disclosed herein is a system for the removal of contaminants from an algae culture. Specifically the system includes the incorporation of a contaminant removal system to remove the contaminants from the algae culture without substantially harming the primary algae type or removing a substantial portion of the primary algae type. The system may include additional components such as, but not limited to, ozone gas for increased sterilization, a device for introducing coagulants and flocculent to a fluid, an ultraviolet light sterilizer, an active carbon filter, an electric dewatering drum filter, a mechanical filtration device, and a centrifuge. Additionally a method for using the systems and apparatus is disclosed.

BRIEF DESCRIPTION OF THE DRAWING FIGURES

A more complete understanding of the present invention may be derived by referring to the detailed description when considered in connection with the following illustrative figures. In the following figures, like reference numbers refer to similar elements and steps throughout the figures.

Elements and steps in the figures are illustrated for simplicity and clarity and have not necessarily been rendered according to any particular sequence or scale. For example, steps that may be performed concurrently or in different order are illustrated in the figures to help to improve understanding of embodiments of the present invention.

The figures described are for illustration purposes only and are not intended to limit the scope of the present disclosure in any way. Various aspects of the present invention may be more fully understood from the detailed description and the accompanying drawing figures, wherein:

FIG. 1 representatively illustrates an exemplary contaminant removal system coupled to an algae v-trough type bioreactor;

Figure 11:
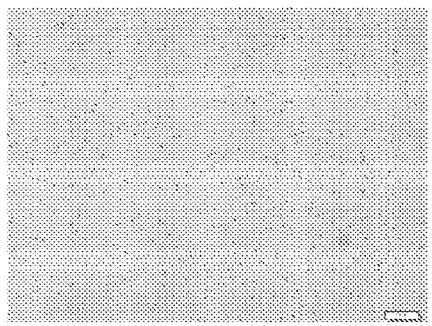
Figure 11:
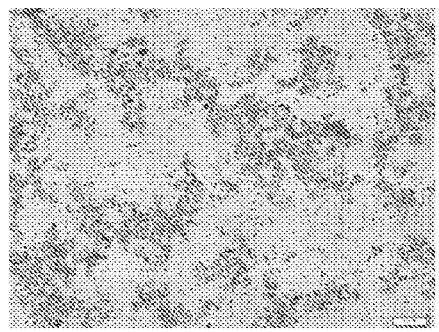
Figure 11:
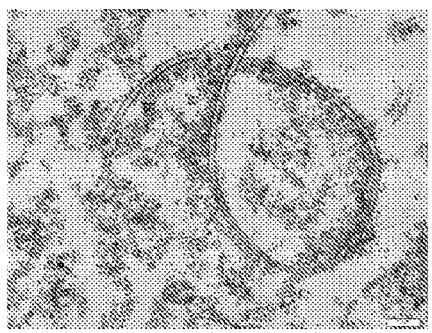
Figure 12:
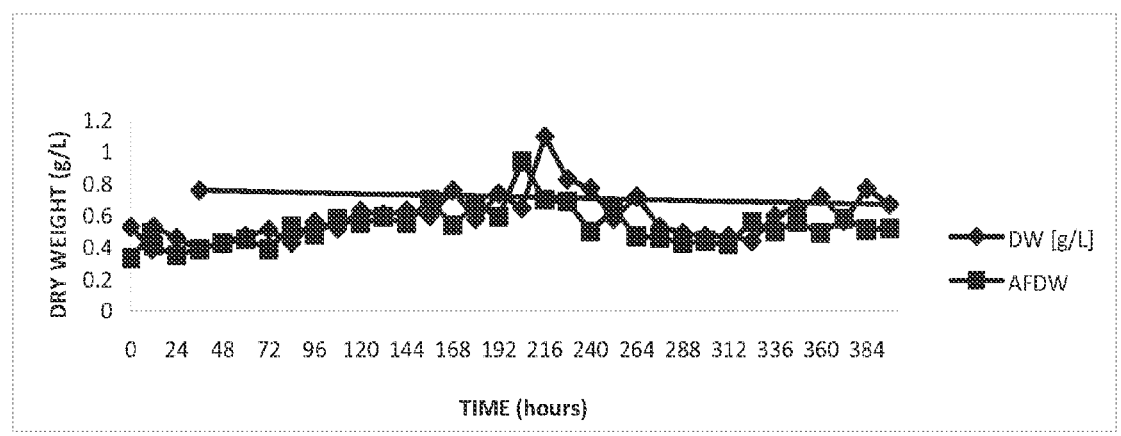

FIGS. 11A, 11B, and 11C are microscopy pictures of contaminant removal system effluent and solid material collected by the contaminant removal system; and FIG. 12 is a graph illustrating the growth of the liquid algae culture treated with ozone gas and the contaminant removal system.

Figure 13:
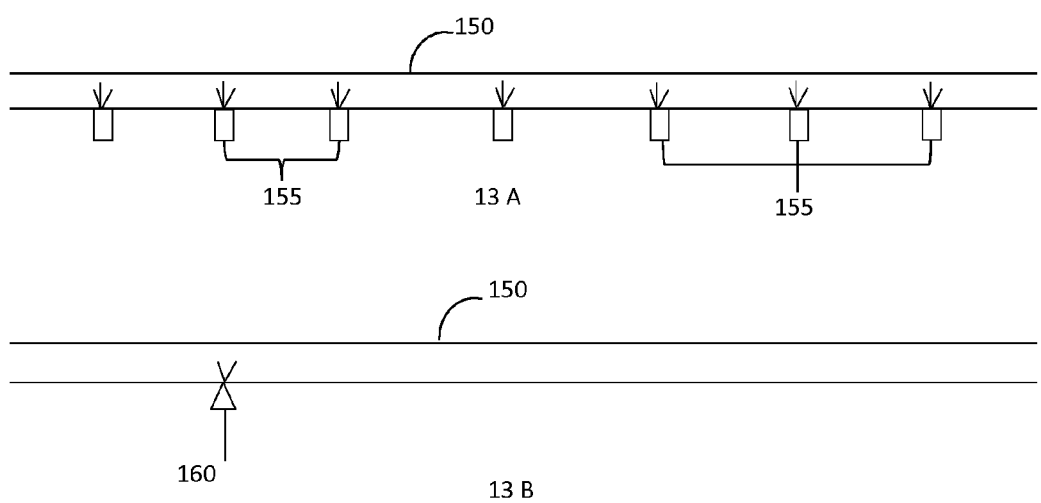

FIGS. 13A and 13B representatively illustrate a return pipe showing a photosynthetically active radiation (PAR) light source disposed along the length of the return pipe and a non-oxidizing gas injector disposed along the length of the return pipe.

DETAILED DESCRIPTION

The present invention may be described in terms of functional block components and various processing steps. Such functional blocks may be realized by any number of components configured to perform the specified functions and achieve the various results. For example, the present invention may employ various process steps, apparatus, systems, methods, etc. In addition, the present invention may be practiced in conjunction with any number of systems and methods for removing contaminants from a vessel such as a bioreactor to promote the growth of an aquatic organism such as an algae culture in the vessel, and the system described is merely one exemplary application for the invention. Various representative implementations of the present invention may be applied to any type of vessel configured to contain a liquid culture of the aquatic organism. Certain representative implementations may include, for example, applying the contaminant removal system to the vessel to promote the growth of the algae culture in the vessel.

The particular implementations shown and described are illustrative of the invention and its best mode and are not intended to otherwise limit the scope of the present invention in any way. For the sake of brevity, conventional manufacturing, connection, preparation, and other functional aspects of the system may not be described in detail. Furthermore, the connecting lines shown in the various figures are intended to represent exemplary functional relationships and/or steps between the various elements. Many alternative or additional functional relationships or physical connections may be present in a practical system.

Various embodiments of the invention provide methods, apparatus, and systems for contaminant removal from a liquid algae culture in a vessel. A detailed description of various embodiments, namely a system and apparatus for contaminant removal from an algae culture in a vessel to promote the growth of a primary algal type in the algae culture, is provided as a specific enabling disclosure that may be generalized to any application of the disclosed system and method in accordance with the various described embodiments.

In various embodiments of the present invention, the primary algae type may comprise any type of algae intended to be grown for harvesting purposes within the algae culture. In some embodiments, the primary algae type may be harvested for use in subsequent processes that may produce valuable products. For example, the primary algae type may be harvested for food, food ingredients, food colorants, food dyes, nutraceuticals such as omega 3, 6, 7, and/or 9, eicosapentaenoic acid (EPA), docosahexaenoic acid (DHA), fertilizer, bioplastics, biofuel, chemical feedstock, pharmaceuticals such as vaccines and/or health maintenance products, and/or fuel. In one embodiment, the primary algae type may comprise a microalgae. Microalgae may be any algae or cyanobacteria species, such as a product-excreting cyanobacteria, with a diameter of less than about 50 microns. Microalgae may have a diameter of about 0.5 microns to about 50 microns. In an exemplary embodiment, the microalgae may be *Nannochloropsis*, *Chlorella*, and/or any other strain with a diameter of less than about 50 microns. In various embodiments, the algae culture containing the primary algae type may be grown in fresh water or salt water. In another embodiment, the primary algae type may comprise microalgae of the genus *Chlorella* and/or any other microalgae strain.

In some embodiments, the primary algae type may be a product-excreting cyanobacteria. For example, the product-excreting cyanobacteria may excrete products such as lipids for use in fuels or bioplastics or other applications. The product-excreting cyanobacteria may be a genetically modified cyanobacteria that is engineered to enhance the production of the product. For example, the cyanobacteria of the genus *Synechocystis, Synechococcus, Arthrospira*, and the like can be genetically modified to excrete desirable products such as alkanes, alcohols, hydrocarbons, and/or hydrogen. Some species of cyanobacteria may excrete compounds such as Geosmin and 2-methylisoborneol (MIB) that may degrade water quality, while other compounds can cause clumping and/or inhibit growth of the cyanobacteria. The presence of cyanobacteria in an algae culture may have direct and/or indirect effects on growth of the algae culture. Cyanobacteria may also be introduced to the culture to induce clumping which may increase the harvesting and/or removal efficiency of the algae from the algae culture.

In various embodiments of the present invention, the contaminant removal system may be used to maintain the culture health for a cyanobacteria product that may express oil or other chemicals. The contaminant removal system may be used to help remove both contaminants and expressed valuable products such as oils and chemicals such that the organic containing valuable products may be separated from unwanted contaminants in a downstream processing step.

The contaminant removal system may promote a longer culture viability for microalgae and/or product-excreting cyanobacteria growth systems such that the length of time that an inoculation may maintain growth may be at least one of longer than 3 days, greater than ten days, and/or greater than 30 days. In one embodiment, the range of culture viability may be from three to 300 days without requiring a reseeding. In one embodiment, reseeding may comprise removing the liquid algae culture from the vessel, cleaning the vessel, and starting a new culture with new growth media and seed (e.g. microalgae). However, a partial seeding may occur where some fresh seed is added to an aged culture at various times within the life of the culture. In one embodiment, the partial seeding may comprise adding fresh microalgae to an aged liquid algae culture in the vessel without removing all the liquid algae culture from the vessel.

Contaminant removal and separation methods may be used to decontaminate liquids such as wastewater, aquarium water for fish, and separating mass or sludge from wastewater to produce a purified liquid. A purified liquid may comprise an originally contaminated liquid to which a contaminating substance has been removed by the application of a substance removal and/or separation method, such as by the present contaminant removal system.

Various contaminant removal and separation systems and methods may comprise mechanical filtration, application of liquid and/or solid chemicals to the liquid, electric dewatering, ultra violet (UV) sterilization, a light-emitting diode apparatus, and foam fractionation methods. The conventional use of contaminant removal and separation methods alone may not effectively improve the health of the algae culture because such conventional methods may remove the primary algae type in addition to contaminants.

The contaminants that may be removed or separated from the liquid algae may comprise any substance found in the algae culture which is directly or indirectly harmful to the primary algae type, such as slowing the growth rate of the primary algae type. For example, the contaminants may comprise, pollutants, growth inhibitors, predators, competitors, bacteria, fecal matter, and detritus. The growth inhibitors may comprise, but are not limited to, linoleic acid, coliform bacteria, fungi, algae metabolites, cell debris, detrital matter, dissolved organic matter, other organic matter, and other micro-particles. In one embodiment, micro-particles may comprise any solids that may be in the range of about 10 to about 1000 microns in diameter. The diameter may be the width of the micro-particle, such as the smallest axis of dimension.

The competitors and predators may comprise, but are not limited to, an invasive algae type other than the primary algae type of the culture, zooplankton that feed on phytoplankton, or other organisms that feed on the primary algae type. The contaminants may also comprise any substances that may be poisonous to the primary algae type, substances that promote growth of predators or competitors, substances that promote growth of organisms that directly reduce growth in the primary algae type, and substances toxic to the primary algae type. In some embodiments, the contaminants may comprise coagulated microalgae cells of the primary algae type. In another embodiment, the contaminants may comprise invasive algae and/or microalgae types such as chain-forming cyanobacteria.

Various representative implementations of the present invention may be applied to any vessel for the cultivation of the liquid algae culture. The liquid algae culture may comprise the algae and a liquid growth medium for providing nutrition to the algae. Certain representative implementations may include, for example, a contaminant removal system for substance removal from the liquid algae culture and releasing at least a portion of the liquid algae culture back into the vessel and/or into a system for harvesting the algae culture.

In an exemplary embodiment, the contaminant removal system according to various aspects of the present invention may comprise an inlet tube, a pump, a gas injector, a substantially vertical chamber, a collection container, and/or an outlet tube. Various embodiments of the present invention may further comprise one or more of a filter, an ultraviolet light sterilizer, a light-emitting diode apparatus, an electric dewatering drum, and a coagulation and flocculation device. One embodiment of the present invention may further comprise a system for harvesting the algae from the liquid algae culture.

The contaminant removal system may comprise systems for applying adsorptive bubble separation methods, such as foam fractionation, to the liquid algae culture. Foam fractionation may generate a foam rich in contaminants, such as dissolved organic matter, or suspended solids from the liquid algae culture. Foam fractionation methods may introduce a gas in the form of small air bubbles into the liquid algae culture, which may create an air/water interface on the surface of the bubbles to which some contaminant particles may be attracted. The contaminant particles may comprise hydrophobic molecules including cell debris that may be attracted to the surface of the bubbles to minimize surface energy in an aqueous suspension. The contaminant particles attracted to the bubble's surface may bond to the bubble's surface and rise with the buoyant bubble towards the top of a substantially vertical chamber of a cylindrical, conical, and/or rectangular flat shape such as one that may contain parallel and/or interleaved sections of bubble floatation chambers such as interspersed or interleaved chambers of a second process. The bubbles may become increasingly dense closer to the top of the substantially vertical chamber and form foam rich in the adsorbed contaminant particles. The foam may be separated from the top of the substantially vertical chamber and removed using any collection method, such as a collection cup or scraper. The cleaned liquid algae culture may be returned to the vessel.

The second process may include the use of ultraviolet (UV) or other light for sterilization and/or destruction of contaminants. In one embodiment, UV or other light sterilization may not substantially harm the primary algae type. For example, UV sterilization may kill less than 20% of the primary algae type. In another embodiment, UV or other light sterilization may kill less than 20% of the primary algae type. In yet another embodiment, UV or other light sterilization may kill less than 5% of the primary algae type.

Collection of the foam from the liquid algae culture may at least one of improve a growth rate and extend a lifetime of the liquid algae culture upon returning the liquid algae culture to the vessel for continued cultivation as compared to the growth rate and the lifetime prior to contaminant removal. For example, in one embodiment, the entire volume of the liquid culture in the vessel may be processed through the contaminant removal system between about 1 to about 100 times per hour to improve the growth rate of the microalgae and/or the cyanobacteria by at least 5%.

Conventionally used foam fractionation methods implemented in fish aquariums are configured to remove substantially all of the algae from the water through foam fractionation with the purpose of improving the health of the fish. The algae present in fish aquariums are typically black brush algae (*Rhodophyta*), brown algae (diatoms), blue green algae (cyanobacteria), *Cladophora*, green spot algae (*Choleochaete orbicularis*) and others. Additionally, conventional foam fractionation methods may remove nutrients such as phosphates, amino acids, and other dissolved organic matter on which algae feed. Solid particles removed by the contaminant removal system may range in size from about 10 to about 1000 microns, such as 20 to 200 microns in diameter, wherein the diameter may be the smallest dimension along any axis.

The number of turnovers that the liquid algae culture may spend within the contaminant removal system may vary according to the size of the liquid algae culture, such as once for a large liquid algae culture to 200 turnovers or more. A turnover may be the number of times the volume of the liquid algae culture cycles through the contaminant removal system over a unit of time, such as minutes, hours and/or days. In one embodiment, the turnover may be calculated as the total culture volume (liters), divided by the water velocity (lpm or lph) going into the contaminant removal system, multiplied by the time the contaminant removal system is actively running on the liquid algae culture. In one embodiment, the contaminant removal system may turnover the liquid algae culture in the range of 10 to 1000 turnovers per day. The turnover rate may range from 10 seconds to 10 hours, where the turnover rate is the time for the full volume of the attached growth reactor to move through the contaminant removal system one time.

In various embodiments of the present invention, the contaminant removal system may be configured to remove contaminants from the liquid algae culture, while leaving at least a substantial portion of the primary algae type remaining in the liquid algae culture. The contaminant removal system may comprise a cylindrical tube or column, such as the substantially vertical chamber, and a collection cup to collect the foam. A gas may be injected into the liquid algae culture, such as with a venturi gas injector or by direct gas injection, at a preselected gas flow rate. The liquid algae culture may be pumped into the substantially vertical chamber in a down-welling or up-welling application at a preselected liquid flow rate. In some embodiments, contaminant removal system may implement adsorptive bubble separation methods to separate and remove mineral ores, macroscopic particles, microscopic particles, surface-inactive ions, surface-inactive molecules, precipitate, and dissolved material that may be first absorbed on colloidal particles. In one embodiment, the contaminant removal system may be optimized to remove contaminants and leave the algae in the liquid algae culture by modifying the geometry of the contaminant removal system, such as the dimensions of the substantially vertical chamber, modifying the state of the gas in the liquid algae culture (i.e., dissolved or dispersed), the velocity of the gas flow rate, and/or the velocity of the liquid flow rate.

Figure 1:
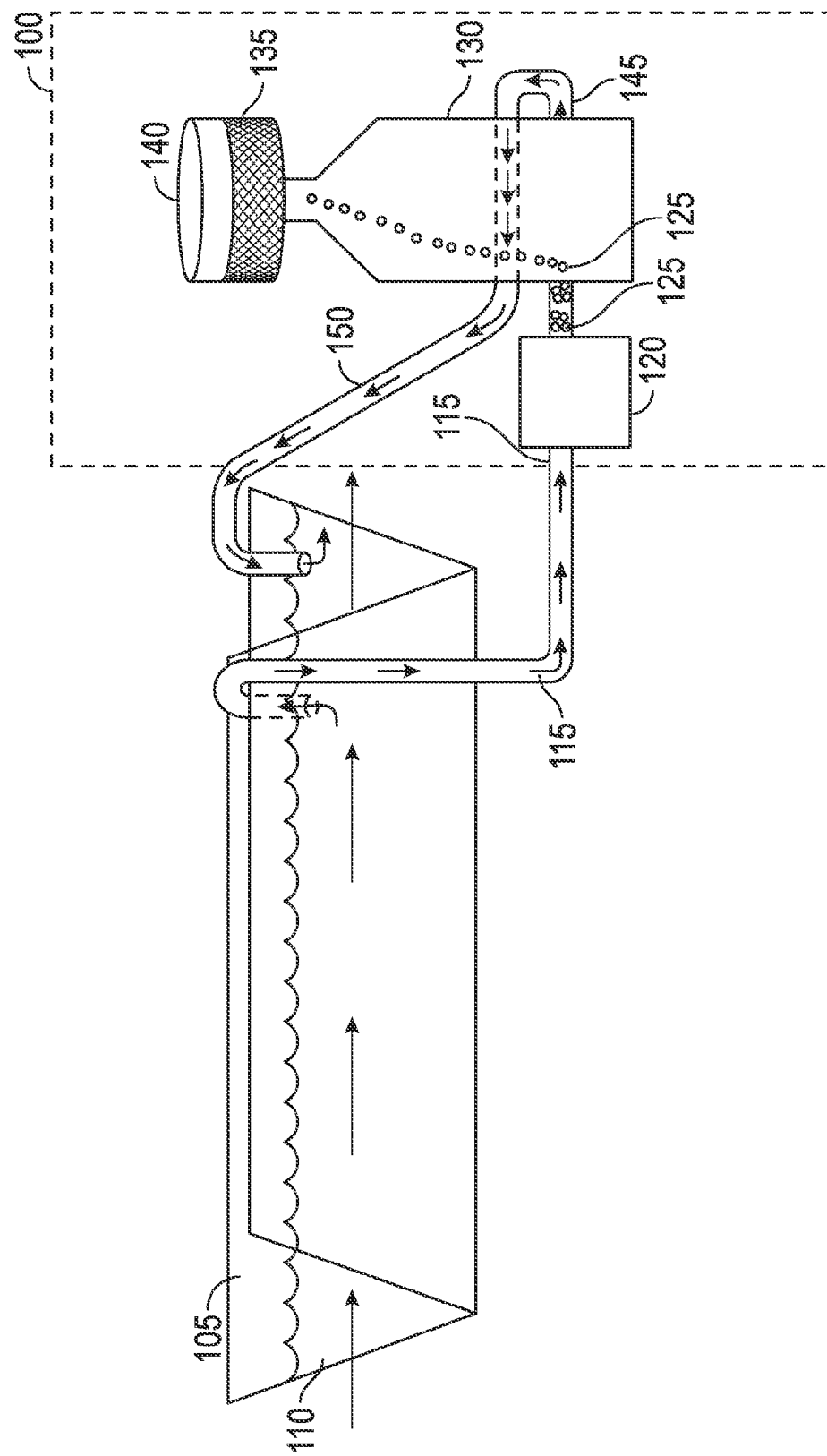

Referring to FIG. 1, an exemplary contaminant removal system 100 may be connected to a vessel 105 that may contain a liquid algae culture 110. The vessel 105 may comprise any apparatus for growing algae in a liquid growth medium (ie, the liquid algae culture 110) for the purpose of harvesting the primary algae type. For example, the vessel 105 may comprise a trough, a V-trough, a pond, a lake, an open growth system, a raceway type pond, a tank, and a photobioreactor (PBR) of any shape or design used to grow microalgae and/or product-excreting cyanobacteria. In one embodiment, the open growth system may comprise a vessel that may be at least partially uncovered. The open growth system may reduce or prevent the ingress of airborne solid matter such as ash. In some embodiments, the airborne solid matter may flow parallel to the open surface of the open growth system. The growth medium of the liquid algae culture 110 may comprise fresh water or salt water either alone or in combination with any nutritional substances to support growth of the algae. In one embodiment, the microalgae concentration in the liquid algae culture 110 may range from about 0.01 g/L to about 100 g/L. In another embodiment, the microalgae concentration in the liquid algae culture 110 may range from about 0.1 g/L to about 10 g/L. In various embodiments of the present invention, any portion of the contaminant removal system 100 may be positioned and/or connected mechanically to any surface of the vessel 105 to contact the liquid algae culture 110 in the vessel 105.

In various embodiments of the present invention, the contaminant removal system 100 may comprise an inlet tube 115 configured to receive the liquid algae culture 110 from the vessel 105. The inlet tube 115 may comprise any suitable material capable of containing the liquid algae culture 110, including but not limited to silicone or polyvinyl chloride piping. In one embodiment, the inlet tube 115 may comprise a material adapted to sustain the liquid algae culture 110 traveling at a high pressure. For example, in one embodiment, the high pressure may be in a range of 10 Pascal (Pa) to 10 MPa. In another embodiment, the high pressure may be in a range of 100 Pa to 1 MPa. In various embodiments, the inlet tube 115 may comprise a material that resists corrosion and/or bacterial growth.

In one embodiment, according to various aspects of the present invention, the inlet tube 115 may be coupled to a pump 120 wherein the pump 120 is configured to receive the liquid algae culture 110 from the vessel 105 and propel the liquid algae culture 110 to a vertical chamber 130 at a preselected liquid flow rate. In one embodiment the pump 120 may be a venturi pump. The venturi pump may comprise a venturi gas injector that may inject gas into the liquid algae culture 110 and mix the gas with the liquid algae culture 110 to form a gas and liquid culture mixture 125 comprising a plurality of small gas bubbles to facilitate the removal of contaminant by a foam fractionation process. In another embodiment, the pump 120 may comprise a conventional water pump and the inlet tube 115 may be coupled to a separate gas injector coupled to the pump 120 and configured to inject the gas into the liquid algae culture 110 in the pump 120 at a preselected gas flow rate. In one embodiment, the separate gas injector may comprise a compressed air cylinder (not shown). The gas and liquid culture mixture 125 may be transferred into a vertical chamber 130 configured to receive the gas and liquid culture mixture 125 from the pump 120. In one embodiment, the gas and liquid culture mixture 125 may enter the vertical chamber 130 at a first end of the vertical chamber 130. The gas and liquid culture mixture 125 may be propelled from the first end of the vertical chamber 130 to a second end of the vertical chamber 130. A foam 135 comprising the contaminants may be generated when the gas and liquid culture mixture 125 travels from the first end to the second end of the vertical chamber 130, as described below.

In some embodiments, the vertical chamber 130 may be a substantially vertical cylindrical column. The vertical chamber 130 may be substantially vertical at any suitable angle relative to the flat ground such that bubbles originating from the bottom of the vertical chamber 130 rise to the top of the vertical chamber 130. For example, the vertical chamber 130 may be completely vertical such that the vertical chamber 130 is at a 90 degree angle as compared to the flat ground. However, the vertical chamber 130 may be at more or less than a 90 degree angle as compared to the flat ground.

In one embodiment, the bubbles formed in the gas and liquid culture mixture 125 by the injected gas may create an interface on the surface of the bubble between the liquid algae culture 110 and the gas to which various particles, solids, and substances, such as contaminants, may form an attraction and/or bond. The bubbles may rise to the top of the vertical chamber 130, carrying the bonded contaminant particles along. At the top of the vertical chamber 130, a plurality of bubbles may form the foam 135 which may be collected in a collection container 140. The collection container 140 may be disposed at the second end of the vertical chamber 130 and configured to collect the foam 135. The collection container 140 may comprise any type of container that may collect the foam 135 from the vertical chamber 130, a foam fractionator, and/or a dissolved air floatation device. For example, the collection container 140 may comprise a cup, tray, tote, basket, and/or a tub. The remaining liquid algae culture 110 may then flow to the outlet tube 145 of the vertical chamber 130.

In some embodiments, the liquid algae culture 110 with reduced contaminants flowing from the outlet tube 145 of the vertical chamber 130 of the contaminant removal system 100 may follow a number of subsequent paths, such as, but not limited to: returning to the vessel 105 through at least one of the outlet tube 145 and/or a return pipe 150; harvesting of the microalgae from the liquid algae culture 110 for further processing, filtering, treatment, dewatering, cleaning, and/or separation; further filtering, treatment, separation or processing by at least one additional method before returning to the vessel 105; and further filtering, treatment, separation or processing by at least one additional method before harvesting or further processing. In one embodiment, the entire volume of the liquid algae culture 110 exiting the vertical chamber 130 may follow a single path. In another embodiment, the volume of liquid algae culture 110 may be split into fractions with the fractions following any combination of multiple paths.

The gas injected into the liquid algae culture 110 by the pump 120, wherein the pump 120 is a venturi pump, or the gas injector may comprise any gas, such as air, ozone, nitrogen, flue gas, and carbon dioxide. The type of gas used may be selected based on any suitable parameter such as the species of algae in the algae culture, the growth stage of the algae, the type of contaminants in the algae culture, and/or the intended use of the contaminant removal system 100. In one embodiment, the use of air and carbon dioxide as the injected gas may operate to remove contaminants from the liquid algae culture 110 by forming bubbles for foam fractionation without substantially harming the microalgae in the liquid algae culture 110. In one embodiment, the gas may remain at least partially undissolved in the liquid algae culture 110 and form the bubbles. In one embodiment, the gas may not substantially harm the microalgae in the liquid algae culture 110 when less than about 10% of the microalgae are killed in one turnover of the liquid algae culture 110 in the contaminant removal system 100. In another embodiment, the gas may not substantially harm the microalgae in the liquid algae culture 110 when less than about 5% of the microalgae are killed. In yet another embodiment, the gas may not substantially harm the microalgae in the liquid algae culture 110 when less than about 1% of the microalgae are killed.

In one embodiment, the use of ozone as the injected gas may not be substantially harmful to the microalgae when ozone is used to remove contaminants and/or sterilize the liquid algae culture 110. For example, the use of ozone as the injected gas in a concentration of approximately 0.01-5.0 milligrams per liter may not be substantially harmful to the microalgae. In one embodiment, ozone may be injected into the liquid algae culture 110 at a concentration of approximately 0.01-1 milligram per liter. In another embodiment, the use of ozone as the injected gas may be beneficial to the microalgae by sterilizing the water through oxidation of organic contaminants while leaving the microalgae substantially unharmed. The use of ozone may kill less than 20% of the microalgae, such as less than 10%, less than 5%, and/or less than 2% of the microalgae. In some embodiments, ozone may adversely affect contaminants to a greater degree than the microalgae and/or the product-excreting cyanobacteria. The injection of ozone in the contaminant removal system 100 may provide continuous removal of organic wastes and simultaneous disinfection of the liquid algae culture 110. Additionally, ozone may be applied at thresholds that may not harm the primary algae type but may simultaneously remove contaminants, such as invasive species of algae. Factors that may be responsible for the effectiveness of the ozone treatment of the liquid algae culture 110 may comprise the contact time of the ozone with the liquid algae culture 110, the concentration of ozone, and/or the ozone demand of the water. In another embodiment, the ozone gas may be injected into the liquid algae culture 110 in the vessel 105 prior to the liquid algae culture 110 entering the pump 120 of the contaminant removal system 100.

In one embodiment, according to various aspects of the present invention, the contaminant removal system 100 may comprise one or more adjustable operating parameters that may be optimized according to any number of factors, such as the growth requirements of the primary algae type, the growth stage of the primary algae type, the zeta potential of the primary algae type, the size of the primary algae type, the pH of the liquid algae culture 110, the extent of coagulation of the algae cells in the liquid algae culture 110, the type of contaminants to be removed from the liquid algae culture 110, the total organic carbon in the liquid algae culture 110, the amount of algal biomass in the liquid algae culture 110, the concentration of algal biomass in the liquid algae culture 110, and the contamination rate of the liquid algae culture 110.

In one embodiment, the adjustable operating parameters may be configured such that the contaminant removal system 100 may remove between about 0.1% to about 99.99% of the total contamination from the liquid algae culture 110 by processing the total liquid algae culture 110 one time. In another embodiment, the adjustable operating parameters may be configured such that the contaminant removal system 100 may remove between about 10% to about 99% of the total contamination from the liquid algae culture 110 by processing the total liquid algae culture 110 one time. For example, the adjustable operating parameters may be configured such that the amount of remaining ash (dirt) in a harvested culture or partial culture from an open algae growth system contains less than about 20% ash such as less than about 10% or less than about 5% ash in the remaining biomass as measured by an ash-free dry weight compared to the non-ash free dry weight.

In another embodiment, the height of the vertical chamber 130 may be selected to optimize the dwell time of the gas in the liquid algae culture 110. The dwell time may be the average time that the liquid algae culture 110 spends within the vertical chamber 130. In one embodiment, the height of the vertical chamber 130 may range from 10 cm to 10 m. In another embodiment, the height of the vertical chamber 130 may range from 0.1 m to 15 m.

In various embodiments, a flow rate of the liquid algae culture 110 through the contaminant removal system 100 may be preselected. The preselected liquid flow rate of the liquid algae culture 110 may be adapted to aggregate the contaminants in the liquid algae culture 110. The flow rate of the liquid algae culture 110 may be controlled by the pump 120. In some embodiments, the preselected liquid flow rate of the liquid algae culture 110 may range from 1 Liters per minute (LPM) to 1,000,000 LPM. In another embodiment, the preselected liquid flow rate of the liquid algae culture 110 may range from 10 LPM to 10,000 LPM.

In various embodiments, a flow rate of the gas injected into the liquid algae culture 110 by the pump 120 may be preselected. The preselected gas flow rate may be adapted to aggregate the contaminants in the liquid algae culture 110. For example, in some embodiments, the preselected gas flow rate may range from 1 standard Liters per minute (SLPM) to 10,000,000 SLPM. In one embodiment, the preselected gas flow rate may range from 100 LPM to 100,000 LPM. In one embodiment, the gas flow rate may range from 2.8 lpm (0.1 scfm) to 2,800,000 lpm (100,000 scfm) for a process with a unit diameter less than 1 in where diameter is defined by the smallest dimension along any axis perpendicular to the direction of flow and may be maintained for at least 20% of the flow length or at the smallest point of a conical shape. Diameter may not describe the inclusion of a smaller connecting pipe. In another embodiment, the gas flow rate may range from 1 scfm to 1000 scfm for an injection point within the skimmer unit with a unit diameter less than 1 m where diameter is defined by the smallest dimension along any axis perpendicular to the direction of flow. The diameter of the pipe may determine the gas velocity range and pressure.

In an exemplary embodiment of the present invention, the diameter of the vertical chamber 130 may be less than 1 m and the height of the vertical chamber may be less than 5 m. In this exemplary embodiment, the liquid flow rate may range from 1 LPM to 10000 LPM and the gas flow rate may range from 100 SLPM to 100,000 SLPM. In one embodiment, the liquid flow rate may range from about 30 LPM to about 500 LMP and the gas flow rate may range from about 1,500 SLPM to about 5,000 SLPM.

In various embodiments of the present invention, the contaminant removal system 100 may support a continuous growth method or extended growth method for growing microalgae. For example, the contaminant removal system 100 may collect the foam 135 continuously for uninterrupted removal of contaminants from the liquid algae culture 110. In one embodiment, the continuous or extended growth method may provide an improved harvest yield of microalgae and may increase the growing efficiency of the microalgae culture by reducing the rate of death of the microalgae and reducing the materials and labor needed to start each new microalgae culture. Contaminant removal by the contaminant removal system 100 may achieve conditioning of the microalgae culture such that the microalgae may resume growth and/or grow to higher densities, which may increase production of each microalgae culture and may reduce costs associated with lost algae cultures. In another embodiment, the contaminant removal system 100 may remove contaminants at a rate which allows the growth rate of the primary algae type in the vessel 105 to maintain a constant algae culture density.

In an exemplary embodiment, the contaminant removal system 100 may at least partially reduce contaminant particles in the liquid algae culture 110 comprising a culture of *Nannochloropsis*, product-excreting cyanobacteria, and/or any other microalgae leaving the culture substantially unharmed. For example, the liquid algae culture 110 exiting the vertical chamber 130 of the contaminant removal system 100 when run continuously for 3 days may contain unharmed *Nannochloropsis* microalgae and a reduced concentration of contaminants. The *Nannochloropsis* microalgae cells exiting the contaminant removal system 100 may exhibit cellular characteristics of being the younger, round, and healthier individual algae cells found in the liquid algae culture 110 that entered the contaminant removal system 100. The contaminants removed from the liquid algae culture 110 and found in the collection container 140 may comprise older, dead, and/or coagulated *Nannochloropsis* microalgae as well as large concentrations of non-algae contaminants measuring approximately 50 microns or less. The microalgae cells in the liquid algae culture 110 exiting the contaminant removal system 100 may continue to grow when placed in a separate tank and monitored for five days. Accordingly, the majority of a culture of *Nannochloropsis* microalgae may successfully travel through the contaminant removal system 100 and may return to the vessel 105 for further culturing, wherein the algae cells of the primary algae type are considered to be in a healthy state with the liquid algae culture 110 having a reduced concentration of contaminants.

Example 1

The effect of treating the liquid algae culture 110 with the contaminant removal system 100 was tested on an algae culture primarily comprising *Nannochloropsis* microalgae grown in a 4.57-m long V-trough reactor (140 degree angle) with algae convection achieved through the use of a 1.5 hp centrifugal pump 340 lpm to rotate the fluid in a clockwise fashion. The reactor width is 1.5 m and the maximum depth at the apex of the central angle is 0.46 m. The liquid volume in the reactor was 1,580 liters (about 427 gallons). The contaminant removal system 100 was run for 12 hours (throughout the night). The *Nannochloropsis* cells run through the contaminant removal system 100 remained viable after the contaminant removal process and continued to grow in the following days. The clean effluent was sent back to the vessel 105 for continued growth and recycling through the contaminant removal system 100.

Figure 7:
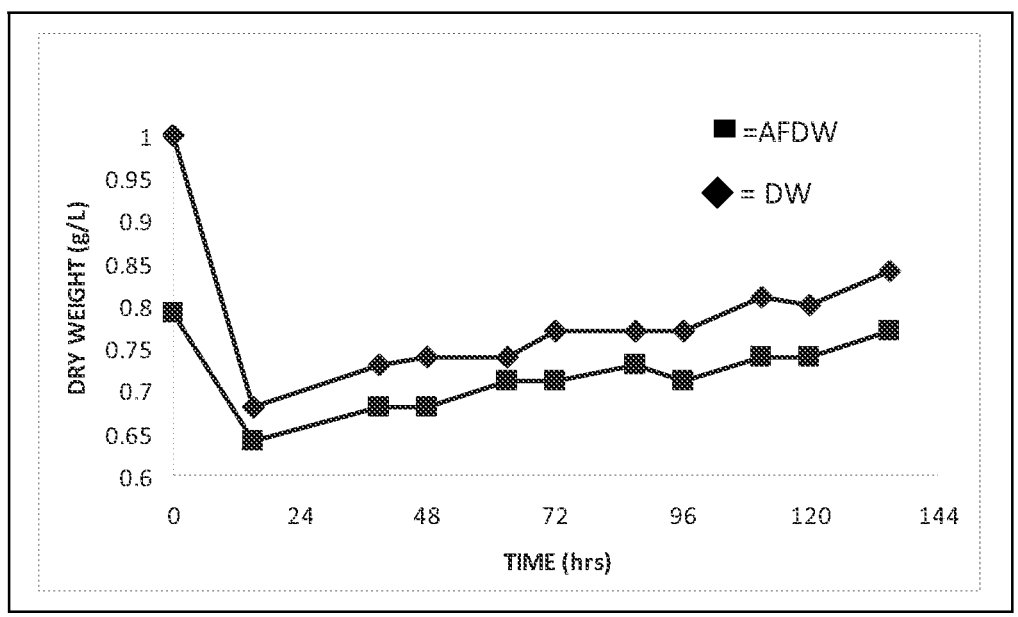
FIG. 7 is a graph illustrating the concentration of ash in a liquid algae culture before and after the use of the contaminant removal system.

The contaminant removal system 100 used in FIG. 7 was a conventional commercially available aquarium protein skimmer adapted for use as a contaminant removal system 100 wherein the protein skimmer has an inlet tube, a pump, a vertical chamber, a collection container, and an outlet tube. Specifically, the contaminant removal system 100 was Aqua-C skimmer EV 2000 from AquaC (referred to as "AquaC"). The AquaC is 101.6 cm (40") tall and has a footprint of 22.86 cm×30.48 (9"×12"). There is a 1.54 cm (1") hose barb for the water input and a 5.08 cm (2") gate valve that controls the flow through the AquaC. The gate valve is 22.86 cm (9") above the bottom of the AquaC. The barb size on the collection cup is 1,905 cm (¾"). The AquaC contains dual threaded air inlets 0.9525 cm (⅜") with 0.635 cm (¼") fittings. The Aqua-C is rated by the manufacturer for 1,892 liters (500 gallon)-7.570 liters (2,000 gallon) reef tanks. The water pump drives the liquid algae culture through the AquaC at 1,570 lph (2000 gallon per hour) is connected to the skimmer via a 1.54 cm (about 0.6") flex tube. In one embodiment, the 0.635 cm (½") air nozzle was configured to be 100% opened during operation. The dual 0.635 cm (¼") air inlets were fully open with approximately 15 Lpm of air for each for a total of 30 Lpm of air. The rotameter that controlled the gas velocity into the AquaC and the pump that fed the AquaC unit were modified such that the rotameter was increased to allow for a higher gas velocity into the AquaC. The pump was a faster flow rate than disclosed by the manufacturer. The inlet pipe diameter for feeding the AquaC water was also modified to a smaller diameter. The air injection port on the skimmer was be set to maximum air injection to create a desired amount of foam fractionation.

The AquaC removed approximately 24% ash (30% average prior to processing, and 6% average ash after processing as determined by a dry weight and ash free dry weight measurement) and removed 16.19% of the NA % *Nannochloropsis* cells from the culture. It is anticipated from experiments that the AquaC may remove between 1 and 25% of the living algae cells from a culture over a 12 hour period when the incoming flow of feed to the AquaC is between about 10-1,000 turnovers per day. The amount of overhead solids removed was 57 liters (10-15 gallons).

The vessel 105 had a volume of about 1,580 liters (427 gallons). The AquaC purified the liquid algae culture 110 in the vessel 105 for 12 hours throughout the night. The turnover time was approximately 4.79 turnovers per hour. The total number of turnovers during the 12 hour period was 58 times.

FIG. 7 shows the dry weight (DW) of a sample of the liquid algae culture 110 harvested at various time points. At each data point, three 200 mL samples of the liquid algae culture 110 were removed from the vessel 105, centrifuged to pellet the solid material, dried, and weighed. The average weight of the triplicate samples provides each data point. An additional step of washing the solid material to remove the ash was performed to obtain the data points for the ash free dry weight (AFDW). FIG. 7 shows that the AquaC was applied to the liquid algae culture 110 after 24 hours. The DW of the liquid algae culture 110 was initially approximately 1.0 g/L and the AFDW of the liquid algae culture 110 was approximately 0.79 g/L. This indicates that approximately 21% of the DW of the liquid algae culture 110 was ash. After the AquaC was applied to the liquid algae culture 110, the ash was reduced to approximately 5-8% of the DW of the liquid algae culture 110. Further, the *Nannochloropsis* cells run through the AquaC remained viable after processing and continued to grow in the following 5 days. The AquaC removed approximately 16.19% of the *Nannochloropsis* cells from the liquid algae culture 110. The amount of solids removed from the liquid algae culture 110 over the 144 hour trial was about 57 L (10-15 gallons).

Prior to processing by the AquaC, the culture showed TEP clumps, diatoms, and competitors to the *Nannochloropsis* microalgae such as unwanted cyanobacteria as observed under a microscope (100× magnification) (not shown). After processing by the AquaC there were a minimal number of clumps and diatoms observed (>90% reduction in occurrence). Accordingly, the AquaC removed non-viable cells, dirt and particulate matter, clumped cells, predators, competitors and other algal species that are larger than *Nannochloropsis* 202-3, which has a size range of 2-6 um.

Example 2

In another trial use of the Aqua-C skimmer EV 2000, the AquaC was modified by installing a 2000 gph pump to operate with a liquid flow rate of 7,570 liters per hour. The air nozzle was run 100% open 0.635 cm (¼" diameter) with a gas flow rate of approximately 20-30 lpm. The AquaC was utilized for 12 hours overnight on a second vessel 105 (15' V-Trough) which was similar to that described in FIG. 7 except the pump horsepower (hp) was operated at a third power (0.5 hp), resulting in a lower circulation velocity. The AquaC was used with a 7,570 liters per hour (2000 gph) pump. The reactor had a volume of 1,580 liters (427 gallons). Accordingly, the turnover rate of the liquid algae culture 110 through the AquaC is approximately 12.5 minutes, wherein the total volume of the liquid algae culture 110 would flow through the process once every 12.5 minutes and would spend approximately 0.25 minutes (dwell time) in the AquaC. Over a 12 hour period, there was an average of about 58 iterations of liquid algae culture 110 into the AquaC. The dwell time was the average residence time that the liquid algae culture 110 spent within the internal volume of the AquaC. The AquaC internal volume is divided by the volumetric flow rate of the incoming liquid algae culture 110 to define an average residence time, therein described as the dwell time.

The gate valve on the return to the vessel 105 was kept 50% open for the duration of the run to create backpressure to promote the foam fractionation of the liquid algae culture 110. The backpressure (adjusts the dwell time in the Aqua-C) is adjusted according to the air injection rate and turnover rate. The dual 0.635-cm (¼") air inlets were fully open with approximately 15 Lpm of air for each for a total of 30 Lpm of air. The air injection port on the Aqua-C is set to maximum air injection to create the desired foam fractionation, thus the air injection ports are wide open. The Aqua-C ran overnight (12 hours) and approximately 5 gallons of overhead solids were collected. The collection appeared to be deep green foam as opposed to the brown sand colored foam observed as described in example 1.

The level of contamination from this vessel 105 was reduced to a level for viable cell culture and algal growth resulting in a reduced amount of overhead solids removed. The use of the Aqua-C reduced the amount of competitors, diatoms, and TEP by more than half as measured by microscope with 100× magnification (not shown). Contamination may be present in all cultures that are open to the external environment. There are levels that may be tolerable for algae production However, the growth rate and population dynamics of the contaminant can quickly surpass levels for viable algae culture. The Aqua-C may reduce the contamination to levels that are tolerable for algae production in the vessel 105. The reactor exhibited a 1.4% reduction in ash content in the dry weight after processing by the Aqua-C. This indicated the removal of total suspended solids (TSS) via the Aqua-C. The reduction of TSS can increase light distribution within the photobioreactor (less light blocking by solids) as well as remove particles that would lead to explosions of contamination populations. The 5-day average of algae growth, after processing by the Aqua-C, increased by approximately 10% from 0.141 gram/Liter-Day (g/L-D) to 0.157 g/L-D.

Example 3

Figure 8:
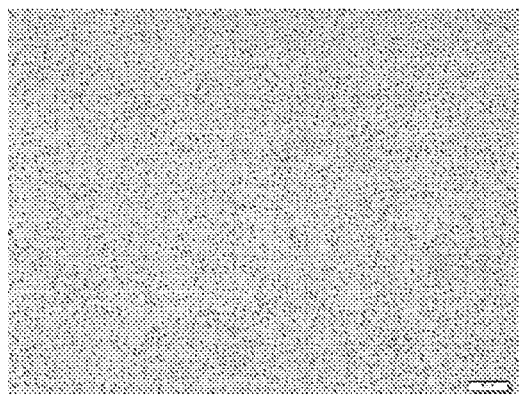
FIGS. 8A and 8B are microscopy pictures of contaminant removal system effluent and solid material collected by the contaminant removal system.
Figure 8:
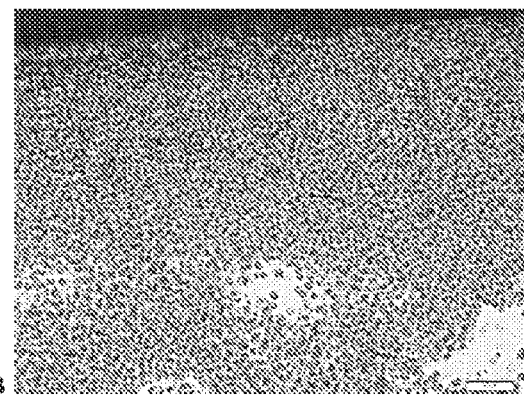
Figure 9:
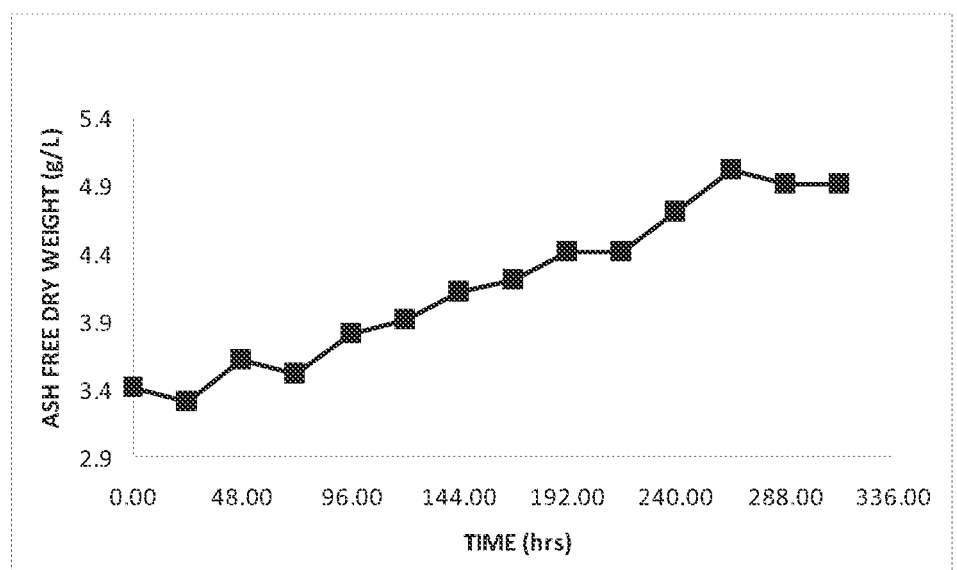
FIG. 9 is a graph illustrating the growth of the liquid algae culture after treatment with the contaminant removal system for 12 hours.

In yet another trial use of the Aqua-C EV 2000, and referring to FIGS. 8 and 9, the Aqua-C was modified to operate with a liquid flow rate of 7,570 liters per hour (2000 gph), the flow rate of air was 20-30 lpm, the volume of the vessel was 114 liters (about 30 gallons). The liquid algae culture 110 was taken from an outdoor contaminated culture and placed into a separate treatment container for processing by the Aqua-C. The Aqua-C was operated for 6 hours resulting in 324 turnovers through the Aqua-C. The Aqua-C was operated with a liquid flow rate of 7,570 liters per hour (about 2050 gph) and the air injection port was run 100% open 0.635 cm (¼" diameter) with a gas flow rate of approximately 20-30 lpm.

FIG. 8A shows a microscopy picture of the liquid algae culture 110 effluent after leaving the skimmer and returning to the vessel 105. This image shows healthy *Nannochloropsis* cells. FIG. 8B shows the contaminants removed from the liquid algae culture 110 by the Aqua-C including unwanted cyanobacteria. The Aqua-C effluent was analyzed for the presence of unwanted cyanobacteria after the treatment and no unwanted cyanobacteria were found. The liquid algal culture 110 was then inoculated into a new vessel 105 and continued to grow (0.2-0.3 g/L day) (see FIG. 9). The culture was not growing and dying off prior to the application of the Aqua-C.

Example 4

In yet another trial use of the Aqua-C skimmer EV 2000, the Aqua-C was configured to have a liquid flow rate of 7570 lph, a liquid algae culture 110 dwell time of 0.25 minutes, a gas injection rate of 20-30 lpm, a turnover rate of 12.5 minutes, and a total of 324 turnovers of the liquid algae culture 110. The Aqua-C removed contamination such as TEPs, bacteria, ciliates, unwanted cyanobacteria and other larger >30 um solids which may include competing algal species and clumped unhealthy algal cells without removing significant amounts of *Nannochloropsis* microalgae (less than 25% of the healthy cells may be sacrificed to retain a healthy liquid algae culture 110 that is viable for continued growth).

Figure 10:
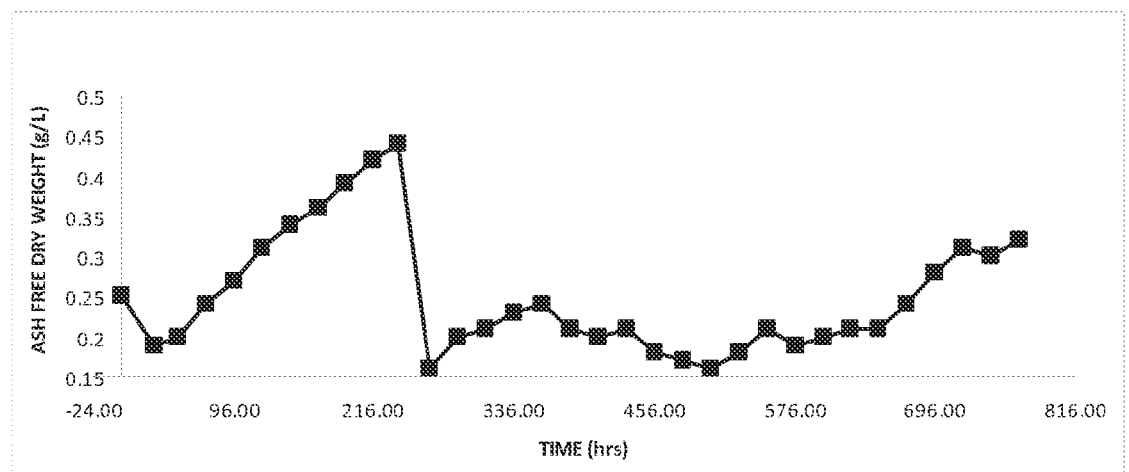
FIG. 10 is a graph illustrating the growth of the liquid algae culture in an indoor vessel after treatment with the contaminant removal system for 6 hours.

Referring to FIG. 10, the skimmer was tested on an indoor vessel 105 without the presence of weather-induced solids accumulation as in the conditions of FIGS. 7-9 (e.g. blowing dirt). The vessel 105 had a volume of 1,580 liters (427 gallons) and was a 15' V-Trough reactor with a 140 degree V shaped bottom that is 5.5° (1.68-m) wide by 15' (4.57 m) long and filled 20 cm from the top giving a volume of about 1,580 liters. The growth rates of the liquid algae culture 110 was (0.03 g/L day; 9 g/m$^2$ day) prior to skimming and decreased in productivity due to contamination and fouling. The growth rate of the liquid algae culture 110 increased to 0.04 g/L day; 12 g/m$^2$-day after skimming for 6 hours. The liquid algae culture 110 was grown indoors under 24 hour fluorescent lighting, which may illustrate a benefit of using the contaminant removal system 100 both inside and outside.

Example 5

In another trial of the Aqua-C skimmer EV 2000, the Aqua-C was configured to have a liquid flow rate of 7570 lph, a liquid algae culture 110 dwell time of 0.25 minutes, a gas injection rate of 20-30 lpm, and a turnover rate of 12.5 minutes. However, the total number of turnovers of the liquid algae culture 110 was 57.6. The Aqua-C was coupled to a 15' (4.57 m) 140 degree V-Trough vessel 105 with a 0.5 HP centrifugal pump for mixing. The vessel 105 has a 140 degree V bottom and is 5.5' (1.68-m) wide by 15' (4.57 m) long and is filled up to 20 cm from the top giving a volume of 1,580 L. The liquid algae culture 110 of *Nannochloropsis* microalgae was grown for over 7 days without harvesting since inoculation.

The Aqua-C was utilized for 12 hours overnight on with the running 0.5 HP centrifugal pump. The gate valve on the return to the trough was kept 50% open for the duration of the run. The dual ¼" air inlets were fully open with approximately 15 lpm of air for each for a total of 30 lpm of air. Approximately 5 gallons of material was collected from the collection container 140 of the Aqua-C. The material in the collection container 140 appeared to be a deep green foam as opposed to the brown sand colored foam observed in another trial. Observations indicated that processing by the Aqua-C reduced the number of competitors and diatom count. TEP was slightly elevated the day after processing but decreased directly thereafter and therefore may have been a result of processing by the Aqua-C. Taking 5-day averages of growth, after skimming the growth in the vessel 105 increased from 0.141 g/L-D to 0.157 g/L-D for a 10% increase.

Example 6

In another trial of the Aqua-C skimmer EV 2000, ozone gas mixed with air was applied to the liquid algae culture 110 in the vessel 105 directly through an air sparger in the vessel 105 or to the air nozzle in the processing by the Aqua-C to provide ozone gas at a concentration of between about 0.01 mg/L to 1.0 mg/L of liquid algae culture 110. The ozone gas was applied to the processing by the Aqua-C to increase the culture viability by applying the ozone in the gas/water interface of the processing by the Aqua-C as opposed to directly in the algae culture, for sterilizing and/or killing the contaminants in the liquid algae culture 110. In each of four runs of this trial, a dying (crashing) liquid algae culture 110 was returned to a growth phase, thus increasing the longevity of the culture, and contaminants were removed.

In a first run of the trial, the contaminated liquid algae culture 110 was disposed in a vessel 105 comprising a Tri-V Trough with 100 degree angles. The ozone gas was directly applied to the liquid algae culture 110 in the vessel 105 through the air sparger for 15 minutes followed by 20 minutes of processing by the Aqua-C. The air pressure was 80 psi and the air injection rate into the ozone unit was 850 lpm at a level of 20% ozone injection. The ozone gas was injected into an airline of the vessel 105 at a flow rate of 42 lph (0.7 lpm). After the ozone treatment, the vessel 105 was processed by the Aqua-C. The rate of gas injection was approximately 15 lpm with 20% ozone. The concentration of microalgae in the vessel 105 was 0.49 g/L prior to processing by the Aqua-C and ozone treatment. The concentration of microalgae in the vessel 105 was 0.41 g/L after processing by the Aqua-C and ozone treatment. The ozone and Aqua-C treatment removed a fraction of the predators and competitors.

The configuration of the injection of ozone into the vessel 105 were 1% Ozone=12.8 g/m$^3$ Ozone in air, 100 g O3/m$^3$=7.8% $O_3$ in air, % Ozone injection into air: 20% Ozone=256 g/m$^3$ Ozone, Air injection: 42 lph or 0.7 lpm, Application Rate: 0.1792 grams per minute, Application Time: 15 minutes, and Total Ozone Applied: 2.688 grams of ozone. The configuration of the Aqua-C was a flow rate of 7570 lph, a dwell time of 0.25 min, gas injection of 15 lpm, turnover rate 1.51 min, and a total turnover of about 20 minutes for 45.3 turnovers with a total of 2.688 grams of ozone applied to the liquid algae culture 110. The Aqua-C was run under the described conditions for 20 minutes. Nutrients (190 mL of nutrients) were added to the vessel 105. The vessel 105 was harvested. Prior to harvest, the bottom of the vessel 105 was brushed and agitation was turned off so the clumps of solid material would settle at the bottom of each vessel 105 where 18.9 L was harvested.

In a second run of the trial applying ozone gas separately to the liquid algae culture 110 from the Aqua-C, the ozone gas was applied to the air sparger of the vessel 105. The liquid algae culture 110 was maintained for about 264 hours. The configuration of the injection of ozone into the vessel 105 was: 1% Ozone=12.8 g/m$^3$ Ozone in air, 100 g O3/m$^3$=7.8% $O_3$ in air, compressed air=80 psi, ozone rotameter=850 lpm, 50% ozone mixed with 50% air (640 g/m$^3$ Ozone), air injection: 42 lph or 0.7 lpm, application rate: 0.448 grams per minute, application time: 15 minutes, total ozone applied: 6.72 grams of ozone, and the vessel was treated with ozone for 20 min. The Aqua-C was applied to the vessel 105 for 30 min. The configuration of the Aqua-C was flow rate: 7570 lph, dwell time: 0.25 min, gas injection: 15 lpm, Turnover rate: 1.51 min, Total Turnovers per treatment: 45.3 turnovers (with a total of 8.96 grams of ozone applied).

In a third run of the trial applying ozone gas separately to the liquid algae culture 110 from the Aqua-C, the ozone gas was applied to the air sparger of the vessel 105. The liquid algae culture 110 was maintained for about 336 hours. The configuration of the injection of ozone into the vessel 105 was: compressed air=80 psi, ozone rotameter=850 lpm, 50% ozone mixed with 50% air (640 g/m$^3$ Ozone), 1% Ozone=12.8 g/m$^3$ Ozone in air, 100 g O3/m$^3$=7.8% $O_3$ in air, air injection: 42 lph or 0.7 lpm, Application Rate: 0.448 grams per minute, Application Time: 10 minutes, Total Ozone Applied: 4.8 grams of ozone, and vessel 105 was treated with ozone for 10 min. The Aqua-C was placed on the vessel 105 after ozone treatment for min. The configuration of the Aqua-C was flow rate: 7570 lph, Dwell Time: 0.25 min, Gas Injection: 15 lpm, Turnover rate: 1.51 min, and Total Turnovers per treatment: 45.3 turnovers (with a total of 0.5 grams of ozone applied).

In a fourth run of the trial, ozone gas was applied to the air nozzle of the Aqua-C. The liquid algae culture 110 was maintained for about 384 hours. The configuration of the injection of ozone into the Aqua-C was: compressed air=80 psi, ozone rotameter=850 lpm, 50% ozone mixed with 50% air (640 g/m$^3$ Ozone), 1% Ozone=12.8 g/m$^3$ Ozone in air, 100 g O3/m$^3$=7.8% $O_3$ in air, air injection flowrate: 15 lpm, application rate: 9.6 grams per minute, total ozone applied: 192 grams of ozone, and the application time of the Aqua-C and ozone treatment was 20 minutes. The configuration of the Aqua-C was flow rate: 7570 lph, dwell time: 0.25 min, gas injection: 15 lpm, turnover rate: 1.51 min, total turnovers per treatment: 30.2 turnovers (with a total of 192 grams of ozone applied).

Referring to FIG. 12, a graph of the dry weight and ash free dry weight of the liquid algae culture 110 of the fourth run of this trial is shown over 384 hours. The liquid algae culture 110 was crashing prior to treatment with the ozone and the Aqua-C. After the treatment, the growth of the liquid algae culture 110 trended upwards.

Example 7

Referring to FIG. 11, the effect of treating a liquid algae culture 110 with the contaminant removal system 100 was tested using a commercially available protein skimmer with air venture injection. This commercially available protein skimmer was model RK10AC-PF from RK-2 Systems (referred to as "RK-2") and is 215.9 cm (85") tall and has a footprint of 38.10 cm×91.44 cm (15"×36"). There is a 1.54 cm (about 0.6") hose barb water input and a 5.08 cm (about 2") gate valve that controls flow though the RK-2. The gate valve is 35.56 cm (14") above the bottom of the RK-2. The RK-2 is rated by the manufacturer for up to 3785.44 L (about 1000 gallon) reef tanks. The volume of the vertical chamber 130 was 71 L. The venturi water pump drives the liquid algae culture 110 through the skimmer at 20,439 lph (5315 gallon per hour) and is connected to the RK-2 via a 1.54 cm (about 0.6") flex tube. The 0.635 cm (¼") air nozzle was configured to be 100% opened during operation. The dual 0.635 cm (¼") air inlets were fully open with approximately 107 Lpm (6435 lph) of air. The gas flow rate was greater than 50 scfm. The air injection port on the skimmer was set to maximum air injection to create a desired amount of foam fractionation.

The RK-2 was coupled to four 4'×4' photobioreactors (vessels 105). The total volume of the liquid algae culture 110 was 368 L. The dwell time of the liquid algae culture 110 in the vertical chamber 130 was 40.3 seconds with approximately 3.44 min turnover rate. The total number of turnovers of the liquid algae culture 110 was approximately 1,256 in three days.

*Nannochloropsis* microalgae were grown in a 121.92 cm×121.92 cm (4'×4') 46 liter flat panel photobioreactor (vessel 105) until the culture was contaminated and clumping. The contaminated algae was added to the culture and diluted 50% with fresh salt water (30 g/l). The culture ran continuously through the skimmer for three days. Samples from the vessel 105 and skimmer collection container 140 were taken on day 3. The vessel 105 contains the liquid algae culture 110 that has been run through the skimmer and the collection container 140 contains the contaminants removed by the protein skimmer from the liquid algae culture 110. FIG. 11A shows a 100× magnification microscopy picture of the liquid algae culture 110 sampled from the vessel 105 that has been cleaned with the protein skimmer with air venturi injection. The cells in FIG. 11A are *Nannochloropsis* microalgae cells with no observed signs of contaminants as the contaminants were non detectable. As a result, the *Nannochloropsis* microalgae cells shown in FIG. 11A may have an increased surface area for gas exchange, receiving light, and nutrient consumptions as compared to the coagulated and contaminated cells shown in FIGS. 11B and 11C.

FIG. 11B shows a 100× magnification microscopy picture of the liquid algae culture 110 that was collected from the top portion of the material collected in the RK-2 collection container 140. FIG. 11B shown contaminants such as solids, coagulated microalgae cells, and unwanted cyanobacteria. FIG. 11C shows a 100× magnification microscopy picture of the liquid algae culture 110 that was collected from the bottom portion of the material collected in the RK-2 collection container 140 that comprises a dense sediment. This material also contains contaminants such as solids, coagulated microalgae cells, and unwanted cyanobacteria.

Example 8

In another trial use of the model RK10AC-PF from RK-2 Systems, *Nannochloropsis* microalgae were grown in a 121.92 cm×121.92 cm (4'×4') 46 liter flat panel photobioreactor (total volume 184 L) until the culture was contaminated. The liquid algae culture 110 was removed and placed into a 184 L vessel 105 with aeration for agitation. The dual 0.635 cm (¼") air inlets were fully open with approximately 107 Lpm (6434.5 lph) of air. The venturi water pump drives the liquid algae culture 110 through the RK-2 at 20,439 Lph (5315 gallon per hour). The volume of the vertical chamber 130 was 72.1 L. The dwell time of the liquid algae culture 110 in the vertical chamber 130 was 40.3 seconds with approximately 1.7 min turnover rate. There total number of turnovers of the liquid algae culture 110 was approximately 60.7 in 60 minutes.

Particles in the liquid algae culture 110 were initially about 20% contamination and 80% *Nannochloropsis* microalgae. After approximately 60 minutes of RK-2 use where the liquid algae culture 110 passed through the RK-2 approximately 60.7 times, the contamination was reduced by 6% to be 14% of the total particles. Contamination was considered to be cells outside the size range of *Nannochloropsis* (2-8 μm).

An automated FlowCAM® instrument for particle size analysis by digital imaging of particles in a continuous flow of fluid was set consider particles that were 2-8 microns in diameter to be "normal" The FlowCAM® instrument considered all particles outside this range to be contamination and yielded a contamination level of 14% of the total particles. As in the microscopy pictures of Example 6, after running the liquid algae culture 110 through the skimmer for 60 minutes, a sample of the liquid algae culture 110 from the vessel 105 showed the *Nannochloropsis* microalgae cells with no signs of contaminants (not shown). The microscopy pictures of the liquid algae culture 110 that were collected from the RK-2 collection container 140 showed solids, coagulated microalgae cells, and unwanted cyanobacteria (not shown).

In one embodiment, according to various aspects of the present invention, the contaminant removal system 100 may be used with a liquid algae culture 110 comprising salt-water. Use of the contaminant removal system 100 in salt-water applications may remove organic compounds from the liquid algae culture 110 before the organic compounds decomposed into waste. In some embodiments, removal of the organic compounds may improve the redox potential of the liquid algae culture 110. The redox potential of the liquid algae culture 110 may regulate a variety of biogeochemical reactions, such as surface charges between elements, and may characterize oxidation-reduction status of surface environments. The redox potential may be determined by measuring the electrochemical potential within the water of the liquid algae culture 110.

In various embodiments, the contaminant removal system 100 may be used with two or more, two to ten, or two to one hundred or more parallel algae growth systems, whereas interconnecting pipes, valves, and controls are used to intermittently switch flow between vessel 105 such that multiple growth systems may be cleaned by each contaminant removal system 100 to reduce the number of units required.

Various implementations of the present invention may be used in conjunction with other devices to promote the purification of the liquid algae culture 110 and/or promote the growth of the primary algae type. In some embodiments, the contaminant removal system 100 may be used with a series of devices in fluid communication which apply different methods of contaminant removal and treatment of the liquid algae culture 110. Disclosed below are a number of exemplary, non-limiting embodiments that may include the contaminant removal system 100 configured for removing contaminants from the liquid algae culture 110. The embodiments of the contaminant removal system 100 described are intended to encompass alternative arrangements of the components of the contaminant removal system 100 in a different order, and/or removal of one or more of the components of the contaminant removal system 100 in which the resulting system would still achieve results substantially similar to the results of the disclosed examples.

In various embodiments of the present invention, referring to FIGS. 13A and 13B, the return path to the vessel 105 may he coupled to a return pipe 150 to carry the liquid algae culture 110 back to the vessel 105 from the contaminant removal system 100 and/or to another device for additional filtering, harvesting and/or other processing. In an exemplary embodiment, the return pipe 150 may include a light source 155 disposed along the length of the return pipe 150 that may expose the algae in the liquid algae culture 110 returning to the vessel 105 (or another device) to Photosynthetically Active Radiation (PAR) during its return to the vessel 105. The light source 155 may comprise, but is not limited to, a plurality of light emitting diodes (LED). The return pipe 150 may also include a gas injector 160, or other device for introducing a gas into the liquid algae culture 110, to introduce a gas such as air, carbon dioxide, or ozone into the liquid algae culture 110 during its return to the vessel 105.

In one embodiment, the return pipe 150 may carry the liquid algae culture 110 to a device for harvesting the microalgae. For example, the return pipe 150 may be coupled to a harvesting device such as a centrifuge that uses gravitational force to separate the growth media from the microalgae and/or the product-excreting cyanobacteria in the liquid algae culture 110. In one embodiment, the harvesting device may be an electric dewatering drum filter and/or other device(s) for separating the microalgae and/or product-excreting cyanobacteria from the growth medium. In one embodiment, the separated microalgae may be returned to a vessel 105 for continued growth. For example, a culture of product-excreting cyanobacteria may experience negative effects from the accumulation of carbon compounds and/or chemicals in the growth medium. The isolated product-excreting cyanobacteria may continue to grow when added to fresh growth media or an existing liquid algae culture 110. In some embodiments the isolated microalgae and/or product-excreting cyanobacteria may be further processed to obtain a target product, such as a phytochemical, chemical, lipid, oil, hydrocarbon, and/or a biofuel. In another embodiment, the growth medium that is separated from the microalgae may be further processed to isolate compounds that have been excreted from the microalgae. For example, the growth medium removed from the harvesting device, such as the centrifuge, may be further purified to isolate a product excreted by the product-excreting cyanobacteria.

In various embodiments of the present invention, the contaminant removal system 100 may be coupled to one or more sensors and control systems that may be employed as an automated control system to control the flow rate of the liquid algae culture 110 entering the contaminant removal system 100, the flow rate or velocity of the gas injected into the liquid algae culture 110, the type of gas to inject into the liquid algae culture 110, and/or the rate of contaminant removal from the collection container 140.

In some embodiments, according to various aspects of the present invention, methods and devices of contaminant removal and fluid treatment that may be used in combination with the contaminant removal system 100 may comprise, but is not limited to: a device configured to introduce coagulants and flocculent into the liquid algae culture 110 which may cause coagulated algae or flocs of algae to form in the liquid algae culture 110 for more efficient removal from water; manipulation of pH to increase or reduce cell clumping; a mechanical filtering device comprising a membrane or media with apertures for allowing only particles of a certain size within the liquid algae culture 110 to pass through the filter; an electric dewatering device comprising charged electrodes which apply an electrical field to a solution to induce movement of water away from solid particles in the liquid algae culture 110 by electrical attraction; an ultra violet (UV) light sterilizer comprising a device providing light of a specific wavelength which breaks down organisms by exposure; an activated carbon filter comprising porous carbon for allowing only particles of a certain size and type within the liquid algae culture 110 to pass through the porous carbon; and a centrifuge configured to apply acceleration to separate matter within the liquid algae culture 110 based on density of the matter.

Figure 2:
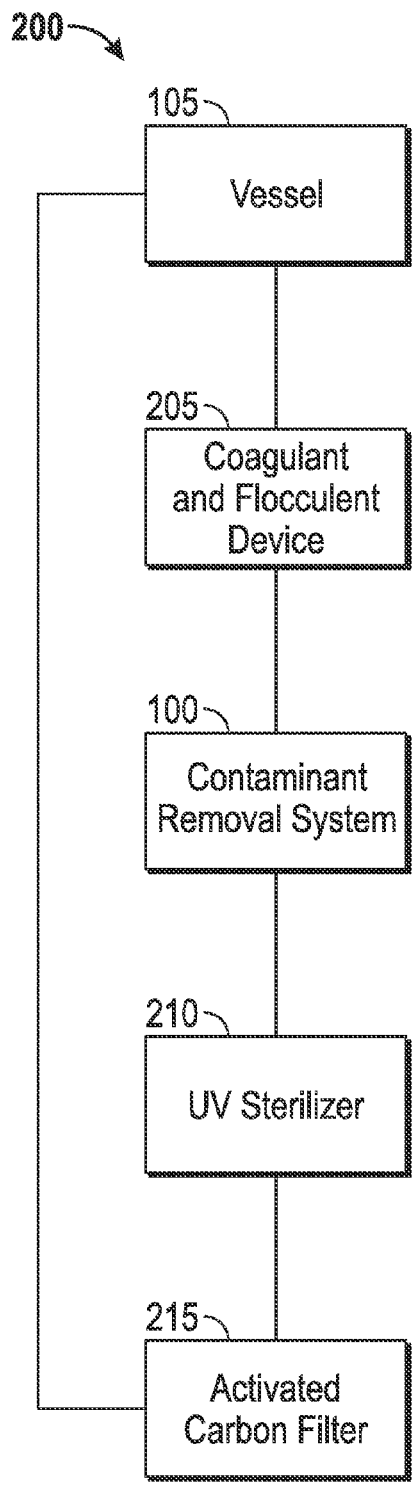
FIG. 2 is a block diagram illustrating an exemplary arrangement of components in the contaminant removal system.

Referring to FIG. 2, in an exemplary embodiment of the present invention 200, the contaminant removal system 100 may be implemented in conjunction with the vessel 105, a device for introducing coagulants and flocculent 205 into the liquid algae culture 110, a UV sterilizer 210, and an activated carbon filter 215. The vessel 105 may be coupled to the coagulant and flocculent device 205 such that the liquid algae culture 110 may flow from the vessel 105 through the coagulant and flocculent device 205. The contaminant removal system 100 may be configured to receive liquid algae culture 110 from the coagulant and flocculent device 205 and may allow for removal of a portion of the liquid algae culture 110 or algae for harvest. The coagulant and flocculent device 205 may at least one of introduce chemicals (flocculating agents) that may contain cationic and/or anionic particles that may cause contaminant particle to clump together for easy separation from the liquid algae culture 110. The coagulant and flocculent device 205 may also provide rapid mixing of the liquid algae culture 110 to promote the formation of the clumps.

The UV sterilizer 210 may be configured to receive at least a portion of the liquid algae culture 110 from the contaminant removal system 100 to expose the liquid algae culture 110 to UV radiation. The activated carbon filter 125 may be configured to receive the liquid algae culture 110 that was exposed to UV radiation from the UV sterilizer 210. The activated carbon filter 215 may fluidly connect to the vessel 105 for return of the liquid algae culture 110 to the vessel 105 for continued growth of the algae culture and/or for harvesting purposes.

Figure 3:
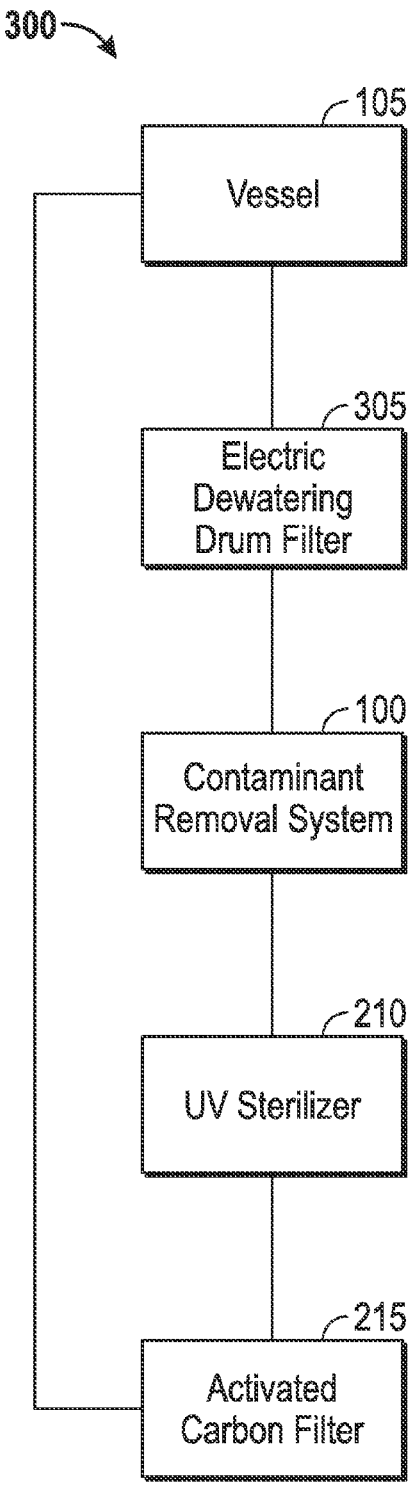
FIG. 3 is a block diagram illustrating another exemplary arrangement of components in the contaminant removal system.

Referring to FIG. 3, in another exemplary embodiment of the present invention 300, the contaminant removal system 100 may be implemented in conjunction with the vessel 105, an electric dewatering drum filter 305, the UV sterilizer 210, and the activated carbon filter 215. The electric dewatering drum filter 305 may be configured to receive the liquid algae culture 110 from the vessel 105. The contaminant removal system 100 may be configured to receive at least partially purified liquid algae culture 110 from the electric dewatering drum filter 305 and may allow for removal of a portion of the liquid algae culture 110 or the algae for harvest. The UV sterilizer 210 may be configured to receive at least a portion of the liquid algae culture 110 from the contaminant removal system 100 to expose the liquid algae culture 110 to UV radiation. The activated carbon filter 215 may be configured to receive the liquid algae culture 110 that was exposed to UV radiation from the UV sterilizer 210. The activated carbon filter 215 may fluidly connect to the vessel 105 for return of the liquid algae culture 110 to the vessel 105 for continued growth of the algae culture and/or for harvesting purposes.

Figure 4:
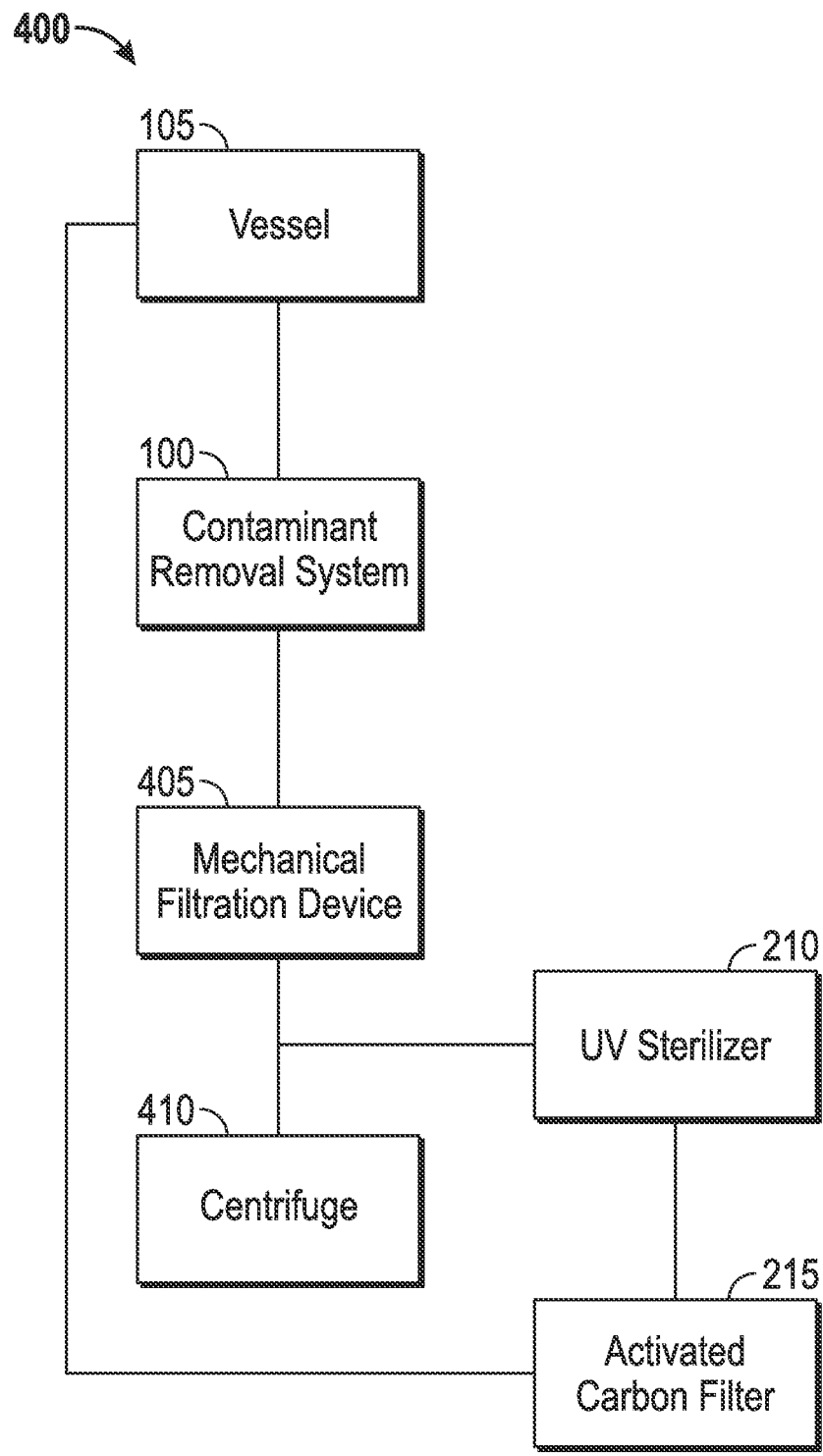
FIG. 4 is a block diagram illustrating yet another exemplary arrangement of components in the contaminant removal system.

Referring to FIG. 4, in yet another exemplary embodiment of the present invention 400, the contaminant removal system 100 may be implemented in conjunction with the vessel 105, a mechanical filtration device 405, a centrifuge 410, the UV sterilizer 210, and the activated carbon filter 215. The contaminant removal system 100 may be configured to receive the liquid algae culture 110 from the vessel 105. The mechanical filtration device 405 may be configured to receive the liquid algae culture 110 from the contaminant removal system 100. The centrifuge 410 may be configured to receive a portion of the liquid algae culture 110 from the mechanical filtration device 405 and allow for removal of a portion of liquid algae culture 110 or the algae for harvest. The UN sterilizer 210 may be configured to receive at least a portion of the liquid algae culture 110 from both the mechanical filtration device 405 and the centrifuge 410. The activated carbon filter 215 may be configured to receive liquid algae culture 110 that was exposed to UV radiation from the UV sterilizer 210. The activated carbon filter 215 may fluidly connect to the vessel 105 for return of the liquid algae culture 110 to the vessel 105 for continued growth of the algae culture and/or for harvesting purposes.

Figure 5:
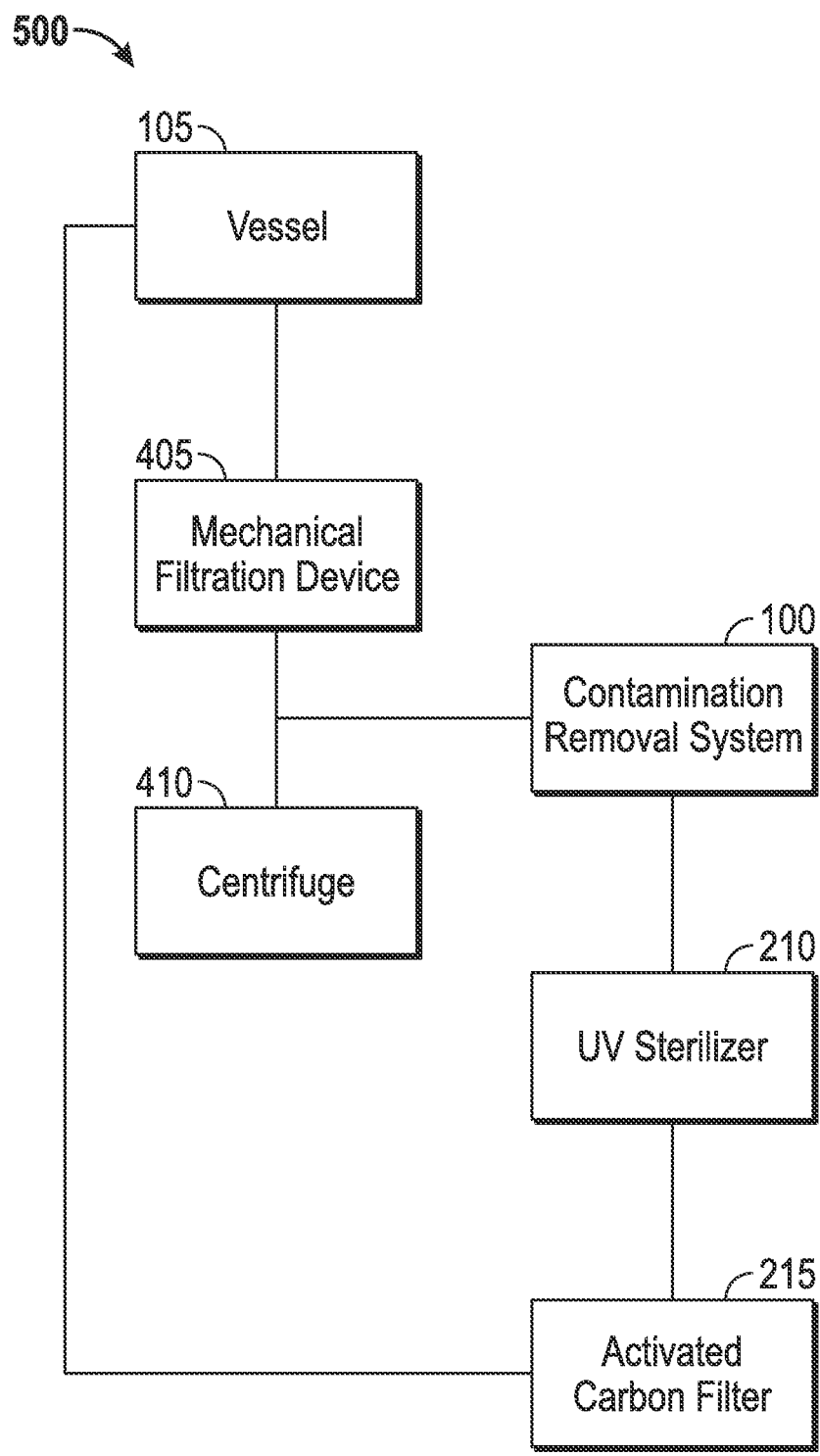
FIG. 5 is a block diagram illustrating yet another exemplary arrangement of components in the contaminant removal system.

Referring to FIG. 5, in yet another exemplary embodiment of the present invention 500, the contaminant removal system 100 may be implemented in conjunction with the vessel 105, the mechanical filtration device 405, the centrifuge 410, the UV sterilizer 210, and the activated carbon filter 215. The mechanical filtration device 405 may be configured to receive the liquid algae culture 110 from the vessel 105. The centrifuge 410 may be configured to receive a portion of the liquid algae culture 110 from the mechanical filtration device 405 and allow for removal of a portion of algae for harvest. The contaminant removal system 100 may be configured to receive the liquid algae culture 110 from the mechanical filtration apparatus 405 and/or the centrifuge 410. The UV sterilizer 210 may be configured to receive at least a portion of the liquid algae culture 110 from the contamination removal system 100. The activated carbon filter 215 may be configured to receive the liquid algae culture 110 that was exposed to UV radiation from the UV sterilizer 210. The activated carbon filter 215 may fluidly connect to the vessel 105 for return of the liquid algae culture 110 to the vessel 105 for continued growth of the algae culture and/or for harvesting purposes.

Figure 6:
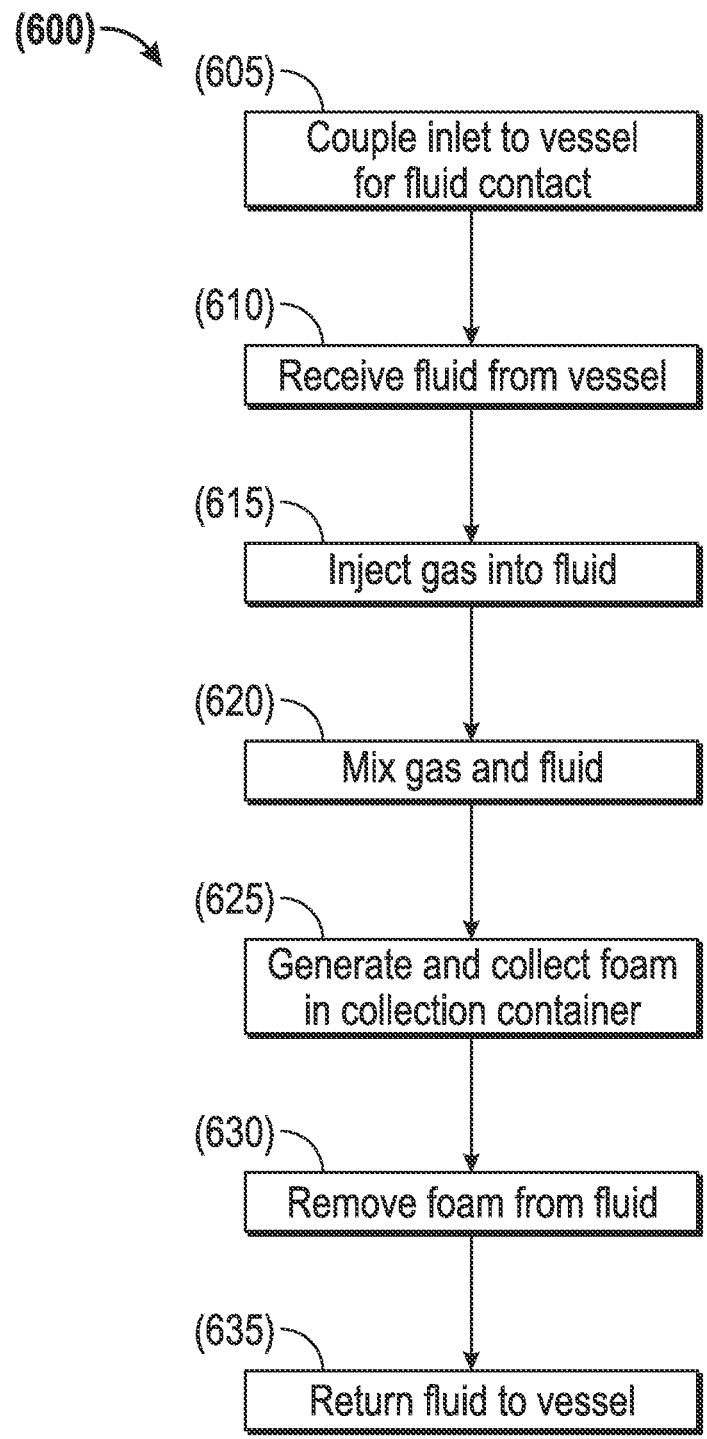
FIG. 6 is a flow chart illustrating an exemplary method of operating the contaminant removal system in conjunction with a vessel.

FIG. 6 representatively illustrates an exemplary method of operation of a contaminant removal system 100 according to various aspects of the present invention (600). The operation of the contaminant removal system 100 may comprise coupling the inlet tube 115 to the vessel 105 such that the inlet may be in contact with the liquid algae culture 110 (605). The contaminant removal system 100 may receive the liquid algae culture 110 from the vessel 105 into the inlet tube 115 (610). The contaminant removal system 100 may pump the liquid algae culture 110 from the inlet tube 115 to the pump 120 using the preselected flow rate. The contaminant removal system 100 may inject a gas into the liquid algae culture 110 using the preselected gas flow rate mix the gas with the liquid algae culture 110 to create gas bubbles (615), mix the gas bubbles and the liquid algae culture 110 to create the gas and liquid culture mixture 125 (620). The gas and liquid culture mixture 125 may be received into the first end of the vertical chamber 130 and generate the foam 135 comprising the contaminants. The foam 135 may travel from the first end to the second end of the vertical chamber 130. The foam 135 may be collected in the collection container 140 (625), wherein the separation and collection of the foam 135 from the gas and liquid culture mixture may improve the growth rate of the microalgae and/or the cyanobacteria. The foam 135 comprising the contaminants may be removed from the liquid algae culture 110, while retaining at least 80% of the primary algae type in the liquid algae culture 110 (630). The purified liquid algae culture 110 may be returned to the vessel 105 through the outlet tube 145 and/or the return pipe 150 for continued growth of the primary algae type and/or for harvesting purposes (635).

The contaminant removal system disclosed above may be used in an exemplary method disclosed herein for removing contaminating substances from a fluid comprising an algae culture and growth medium. The method may comprise a contaminant removal system receiving fluid from a vessel configured for growing a primary algae type in an aquaculture for harvesting purposes, removing contaminating substances from the fluid with the components of the contaminant removal system while retaining at least 80% of the primary algae type in the fluid, and returning the fluid exiting the contaminant removal system to the algae culturing vessel. The contaminant removal system may comprise at least the contaminant removal system 100 disclosed above, and may further comprise any of the systems or system components disclosed above to remove contaminating substances from the fluid. The method may further comprise the additional step of removing a portion of the fluid or algae from a component of the contaminant removal system for algae harvest. The method may also further comprise the additional step of controlling aspects of the contaminant removal system including the flow rate of fluid into the contaminant removal system, the rate of gas injection, the type of gas injected, and the rate of contaminant removal, through an automated sensors and controls system.

As disclosed above with the contaminant removal systems, the method may treat any portion of the fluid from the algae culturing vessel to achieve the desired level of contaminant removal, including treating up to 100% of the fluid from the algae culturing vessel. In some embodiments, the method may further comprise the step of treating the fluid with a wash, such as, but not limited to fresh water, solvent, or a pre-treatment solution to prepare the fluid or algae for a subsequent process such as, but not limited to, extraction and/or harvest.

In one exemplary embodiment of a method for removing contaminating substances, *Nannochloropsis* microalgae may be grown in a saltwater medium within a V-trough growing vessel. A portion of the algae culture containing fluid may flow or be pumped from the V-Trough to a contaminant removal system, wherein the fluid may be mixed with an injected gas, such as air, carbon dioxide, or ozone at approximately 1-50 scfm. The fluid and gas mixture may be transferred into a vertical water chamber where the gas bubbles and particles adsorbed to the gas bubbles may rise to the top of the vertical water chamber and create a foam rich in contaminants from the fluid. The fluid may flow through the contaminant removal system at approximately 1-45 gpm. The foam may collect in a collection tote and may be removed from the contaminant removal system. The remaining fluid containing 80% or more of the *Nannochloropsis* microalgae that entered the contaminant removal system may exit the vertical water chamber through an outlet and/or a return pipe and may be recirculated to the V-Trough growing vessel to rejoin the algae culture.

In some embodiments, the method may further comprise subjecting the fluid containing the algae culture to further processing, harvesting, treatment or separation processes or devices such as, but not limited to coagulation, flocculation, pH manipulation, filtering, dewatering, UV sterilization, and/or centrifugation, before entering the contaminant removal system as described in the exemplary systems disclosed above. In some embodiments, the method may further comprise subjecting the algae culture medium fluid to further processing, harvesting, treatment or separation processes or devices such as, but not limited to coagulation, flocculation, pH manipulation, filtering, dewatering, UV sterilization, and/or centrifugation, after exiting the contaminant removal system as described in the exemplary systems disclosed above. In further embodiments, the method comprises a combination of further processes before and after the fluid enters the contaminant removal system.

In one exemplary embodiment of a method for increasing the growth rate of the liquid algae culture 110 in the vessel 105, wherein the microalgae culture comprises microalgae cells and contaminants, the method comprises coupling the contaminant removal system 100 to the vessel 105 containing the liquid algae culture 110, wherein the growth rate of the microalgae cells is progressively slowing; processing the liquid algae culture 110 in the vessel through the contaminant removal system 100, wherein at least a portion of the contaminants are removed during processing; and returning at least a portion of the processed liquid algae culture 110 to the vessel 105 at least 10 times in a 24 hour period, wherein the portion of the liquid algae culture 110 returned to the vessel exhibits an increase in growth rate of the microalgae cells of at least 5%. In one embodiment, the method for increasing the growth rate of the liquid algae culture 110 in the vessel 105 may remove the contaminants by foam fractionation. The contaminant removal system 100 may inject a gas into the liquid algae culture 110 at a flow rate of approximately 1 SLPM to approximately 10,000,000 SLPM. The flow rate of the liquid algae culture 110 through the contaminant removal system 100 may be from approximately 1 lpm to approximately 1,000,000 lpm.

In one exemplary embodiment of a method for improving the viability of the liquid algae culture 110 in the vessel 105, wherein the liquid algae culture 110 comprises microalgae cells and contaminants, the method comprises: coupling the contaminant removal system 100 to the vessel 105 containing the liquid algae culture 110, wherein the growth rate of the microalgae cells is progressively slowing; processing the liquid algae culture 110 in the vessel 105 through the contaminant removal system 100, wherein at least a portion of the contaminants are removed during processing; and returning at least a portion of the processed liquid algae culture 110 to the vessel 105 at least 10 times in a 24 hour period, wherein the portion of the liquid algae culture 110 returned to the vessel 105 exhibits an increase in the lifetime of the liquid algae culture 110 of at least 5 days as compared to the lifetime of the liquid algae culture 110 without processing. In one embodiment, the method for increasing the growth rate of the liquid algae culture 110 in the vessel 105 may remove the contaminants by foam fractionation. The contaminant removal system 100 may inject a gas into the liquid algae culture 110 at a flow rate of approximately 1 SLPM to approximately 10,000,000 SLPM. The flow rate of the liquid algae culture 110 through the contaminant removal system 100 may be from approximately 1 lpm to approximately 1,000,000 lpm.

In the foregoing description, the invention has been described with reference to specific exemplary embodiments. Various modifications and changes may be made, however, without departing from the scope of the present invention as set forth, The description and figures are to be regarded in an illustrative manner, rather than a restrictive one and all such modifications are intended to be included within the scope of the present invention. Accordingly, the scope of the invention should be determined by the generic embodiments described and their legal equivalents rather than by merely the specific examples described above. For example, the steps recited in any method or process embodiment may be executed in any appropriate order and are not limited to the explicit order presented in the specific examples. Additionally, the components and/or elements recited in any system embodiment may be combined in a variety of permutations to produce substantially the same result as the present invention and are accordingly not limited to the specific configuration recited in the specific examples.

Benefits, other advantages and solutions to problems have been described above with regard to particular embodiments. Any benefit, advantage, solution to problems or any element that may cause any particular benefit, advantage or solution to occur or to become more pronounced, however, is not to be construed as a critical, required or essential feature or component.

The terms "comprises", "comprising", or any variation thereof, are intended to reference a non-exclusive inclusion, such that a process, method, article, composition, system, or apparatus that comprises a list of elements does not include only those elements recited, but may also include other elements not expressly listed or inherent to such process, method, article, composition, system, or apparatus. Other combinations and/or modifications of the above-described structures, arrangements, applications, proportions, elements, materials or components used in the practice of the present invention, in addition to those not specifically recited, may be varied or otherwise particularly adapted to specific environments, manufacturing specifications, design parameters or other operating requirements without departing from the general principles of the same.

The present invention has been described above with reference to an exemplary embodiment. However, changes and modifications may be made to the exemplary embodiment without departing from the scope of the present invention. These and other changes or modifications are intended to be included within the scope of the present invention.

The invention claimed is:

1. A system for removing substances from a liquid culture in a vessel comprising a growth medium and at least one of a microalgae and a cyanobacteria, comprising:
    an inlet tube coupled to the vessel configured to receive the liquid culture from the vessel;
    a pump coupled to the inlet tube, wherein the pump is configured to receive the liquid culture and propel the liquid culture at a preselected liquid flow rate;
    a gas injector coupled to the pump and configured to inject a gas into the liquid culture in the pump at a preselected gas flow rate, and to mix the gas with the liquid culture in the pump to produce a gas and liquid culture mixture;
    a substantially vertical chamber coupled to the pump and configured to receive the gas and liquid culture mixture from the pump at a first end of the substantially vertical chamber, wherein a foam comprising a substance is generated at a second end of the substantially vertical chamber;
    a collection container disposed at the second end of the vertical chamber configured to separate and collect the foam; and
    a return pipe coupled to an outlet of the substantially vertical chamber and the vessel, the return pipe comprising a photosynthetically active radiation (PAR) light source disposed along the length of the return pipe and configured to apply PAR to the interior of the return pipe.

2. The system of claim 1, further comprising a valve configured to adjust the preselected liquid flow rate.

3. The system of claim 2, wherein the preselected liquid flow rate is from approximately 1 lpm to approximately 1,000,000 lpm.

4. The system of claim 2, wherein the preselected liquid flow rate is from approximately 10 lpm to approximately 10,000 lpm.

5. The system of claim 1, further comprising a valve configured to adjust the preselected gas flow rate to promote the aggregation of the contaminants in the liquid culture.

6. The system of claim 2, wherein the preselected gas flow rate is from approximately 1 SLPM to approximately 10,000,000 SLPM.

7. The system of claim 2, wherein the preselected gas flow rate is from approximately 100 SLPM to approximately 100,000 SLPM.

8. The system of claim 1, wherein the gas injector is configured to inject gas which remains at least partially undissolved in the liquid culture and forms bubbles.

9. The system of claim 1, wherein the gas is at least one of air, ozone, nitrogen, flue gas, and carbon dioxide.

10. The system of claim 1, further comprising an ultraviolet light sterilizer applied to the substantially vertical chamber and adapted to sterilize the gas and liquid culture mixture.

11. The system of claim 1, further comprising a harvesting device coupled to the outlet.

12. The system of claim 11, wherein the harvesting device is coupled to at least one of the substantially vertical chamber and the vessel.

13. The system of claim 1, wherein the harvesting device comprises at least one of a filter, a centrifuge, and an electric dewatering drum filter.

14. The system of claim 1, wherein PAR light source comprises at least one light emitting diode (LED).

15. A system for removing substances from a liquid culture in a vessel comprising a growth medium and at least one of a microalgae and a cyanobacteria, comprising:

an inlet tube coupled to the vessel and configured to receive the liquid culture from the vessel;

a pump coupled to the inlet tube, wherein the pump is configured to receive the liquid culture and propel the liquid culture at a preselected liquid flow rate;

a gas injector coupled to the pump and configured to inject a gas into the liquid culture in the pump at a preselected gas flow rate and to mix the gas with the liquid culture in the pump to produce a gas and liquid culture mixture;

a substantially vertical chamber coupled to the pump and configured to receive the gas and liquid culture mixture from the pump at a first end of the vertical chamber, wherein a foam comprising a substance is generated at a second end of the substantially vertical chamber;

a collection container disposed at the second end of the vertical chamber configured to separate and collect the foam; and a return pipe coupled to an outlet of the substantially vertical chamber and the vessel, the return pipe comprising a non-oxidizing gas injector disposed along the length of the return pipe and configured to inject non-oxidizing gas into the interior of the return pipe.

16. The system of claim 15, wherein the non-oxidizing gas comprises at least one of air and carbon dioxide.

17. The system of claim 15, further comprising a harvesting device coupled to the outlet.

18. The system of claim 17, wherein the harvesting device comprises at least one of a centrifuge and an electric dewatering drum filter.

19. The system of claim 17, wherein the harvesting device is coupled to at least one of the substantially vertical chamber and the vessel.

* * * * *